United States Patent [19]

Wozney et al.

[11] Patent Number: 5,661,007
[45] Date of Patent: Aug. 26, 1997

[54] BONE MORPHOGENETIC PROTEIN-9 COMPOSITIONS

[75] Inventors: John M. Wozney; Anthony J. Celeste, both of Hudson, Mass.

[73] Assignee: Genetics Institute, Inc., Cambridge, Mass.

[21] Appl. No.: 50,132

[22] PCT Filed: Jun. 25, 1992

[86] PCT No.: PCT/US92/05374

§ 371 Date: Apr. 22, 1993

§ 102(e) Date: Apr. 22, 1993

[87] PCT Pub. No.: WO93/00432

PCT Pub. Date: Jan. 7, 1993

Related U.S. Application Data

[63] Continuation-in-part of Ser. No. 720,590, Jun. 25, 1991, abandoned.

[51] Int. Cl.$^6$ .................... C12N 15/12; C12N 15/79; C07K 14/51; A61K 38/18

[52] U.S. Cl. .............. 435/69.4; 435/325; 435/252.3; 435/320.1; 435/358; 435/360; 435/364; 435/365; 435/365.1; 514/12; 530/399; 536/23.51; 930/210

[58] Field of Search ................... 424/484, 486; 514/12; 530/399; 930/210; 435/69.4, 240.2, 252.3, 320.1; 536/23.51, 24.31

[56] References Cited

U.S. PATENT DOCUMENTS

| | | | |
|---|---|---|---|
| 4,294,753 | 10/1981 | Urist | 530/395 |
| 4,434,094 | 2/1984 | Seyedin et al. | 530/416 |
| 4,455,256 | 6/1984 | Urist | 530/350 |
| 4,563,350 | 1/1986 | Nathan | 424/95 |
| 4,608,199 | 8/1986 | Caplan et al. | 530/414 |
| 4,619,989 | 10/1986 | Urist | 530/417 |
| 4,627,982 | 12/1986 | Seyedin et al. | 424/95 |
| 4,681,763 | 7/1987 | Nathanson | 424/95 |
| 4,737,578 | 4/1988 | Evans | 530/350 |
| 4,761,471 | 8/1988 | Urist | 530/350 |
| 4,774,228 | 9/1988 | Seyedin | 514/21 |
| 4,774,322 | 9/1988 | Seyedin | 530/353 |
| 4,789,732 | 12/1988 | Urist | 530/350 |
| 4,795,804 | 1/1989 | Urist | 530/350 |
| 4,798,885 | 1/1989 | Mason | 530/350 |
| 4,804,744 | 2/1989 | Sen | 530/350 |
| 4,810,691 | 3/1989 | Seyedin | 514/2 |
| 4,843,063 | 6/1989 | Seyedin | 514/2 |
| 4,886,747 | 12/1989 | Derynck | 435/69.4 |
| 4,968,590 | 11/1990 | Kuberasampath et al. | 530/326 |
| 5,011,691 | 4/1991 | Oppermann | 424/423 |
| 5,106,626 | 4/1992 | Parsons et al. | 424/423 |
| 5,108,753 | 4/1992 | Kuberasampath | 424/422 |

FOREIGN PATENT DOCUMENTS

| | | | |
|---|---|---|---|
| 2 017466 | 5/1990 | Canada | C12N 15/16 |
| 33 6760 | 6/1989 | European Pat. Off. | C07K 7/00 |
| 4 165 78A2 | 5/1990 | European Pat. Off. | C12N 15/00 |
| 4 094 72 A1 | 11/1990 | European Pat. Off. | C12N 15/12 |
| WO90/03733 | 4/1990 | WIPO | A01N 63/02 |
| WO91/02744 | 3/1991 | WIPO | C07K 15/06 |
| WO91/05802 | 5/1991 | WIPO | C07K 15/00 |
| WO91/18047 | 11/1991 | WIPO | |
| WO92/07073 | 4/1992 | WIPO | C12N 15/00 |
| WO92/07004 | 4/1992 | WIPO | C07K 15/06 |
| WO93/04692 | 3/1993 | WIPO | A61K 37/02 |
| WO93/05751 | 4/1993 | WIPO | |

OTHER PUBLICATIONS

Wozney et al, pp. 725–748 in Handbook of Exp. Pharm., vol. 107 (Springer-Verlag, Berlin, 1993).
Urist et al., *Science* 220: 680–686 (1983).
Luyten et al., *The Journal of Biological Chemistry* 264(23):13377–13380 (1989).
Sampath et al., *Proc. Natl Acad. Sci* 84:7109–7113 (1987).
Ozkaynak et al., *The EMBO Journal* v.9 No. 7:2085–2093 (1990).
Hammonds et al., *Molecular Endocrinology* 5:149–155 (1991).
Celeste et al., *J. of Bone Mineral Res.* v.9 suppl. 5136 (1994).
Celeste et al "Identification of Transforming Growth Factor β Family Members . . . ", *PNAS* 87:9843–9847 (Dec. 1990).
Wozney et al, "Novel Regulators of Bone Formation . . ." *Science* 242:1528–1534 (Dec. 1988).
Burt et al, "Evolutionary Grouping of the Transforming Growth Factor–βSuperfamily", *BBRC* 184(2):590–595 (Apr. 1992).
Wozney et al, "Growth Factors Influencing Bone Development", *J. Cell Sci. Suppl.* 13:149–156 1990.
Wang et al, "Recombinant Human Bone Morphogenetic Protein . . ." *PNAS* 87:2220–2224 (Mar. 1990).

*Primary Examiner*—Stephen G. Walsh
*Attorney, Agent, or Firm*—Ellen J. Kapinos; Thomas J. DesRosier

[57] ABSTRACT

Purified bone morphogenetic protein-9 (BMP-9) proteins and processes for producing them are disclosed. The proteins may be used in the treatment of bone and cartilage defects and in wound healing and related tissue repair.

14 Claims, 8 Drawing Sheets

Figure 1A

```
          10         20         30         40         50         60         70
CATTAATAAA TATTAAGTAT TGGAATTAGT GAAATTGGAG TTCCTTGTGG AAGGAAGTGG GCAAGTGAGC
          80         90        100        110        120        130        140
TTTTTAGTTT GTGTCGGAAG CCTGTAATTA CGGCTCCAGC TCATAGTGGA ATGGCTATAC TTAGATTTAT
         150        160        170        180        190        200        210
GGATAGTTGG GTAGTAGGTG TAAATGTATG TGGTAAAAGG CCTAGGAGAT TTGTTGATCC AATAAATATG
         220        230        240        250        260        270        280
ATTAGGGAAA CAATTATTAG GGTTCATGTT CGTCCTTTTG GTGTGTGGAT TAGCATTATT TGTTTGATAA
         290        300        310        320        330        340        350
TAAGTTTAAC TAGTCAGTGT TGGAAAGAAT GGAGACGGTT GTTGATTAGG CGTTTTGAGG ATGGGAATAG
         360        370        380        390        400        410        420
GATTGAAGGA AATATAATGA TGGCTACAAC GATTGGGAAT CCTATTATTG TTGGGGTAAT GAATGAGGCA
         430        440        450        460        470        480        490
AATAGATTTT CGTTCATTTT AATTCTCAAG GGGTTTTTAC TTTTATGTTT GTTAGTGATA TTGGTGAGTA
         500        510        520        530        540        550        560
GGCCAAGGGT TAATAGTGTA ATTGAATTAT AGTGAAATCA TATTACTAGA CCTGATGTTA GAAGGAGGGC
         570        580        590        600    609        618
                                                     >    ___  ___  ___
TGAAAAGGCT CCTTCCCTCC CAGGACAAAA CCGGAGCAGG GCCACCCGG ATG  TCC  CCT  GGG
                                                      M    S    P    G
```

```
    627              636              645              654              663              672
___ ___ ___ ___ ___ ___ ___ ___ ___ ___ ___ ___ ___ ___ ___ ___ ___ ___
GCC TTC CGG GTG GCC CTG CTC CCG CTG TTC CTG CTG GTC TGT GTC ACA CAG CAG
 A   F   R   V   A   L   L   P   L   F   L   L   V   C   V   T   Q   Q 681              690              699              708              717              726
___ ___ ___ ___ ___ ___ ___ ___ ___ ___ ___ ___ ___ ___ ___ ___ ___ ___
AAG CCG CTG CAG AAC TGG GAA CAA GCA TCC CCT GGG GAA AAT GCC CAC AGC TCC
 K   P   L   Q   N   W   E   Q   A   S   P   G   E   N   A   H   S   S 735              744              753              762              771              780
___ ___ ___ ___ ___ ___ ___ ___ ___ ___ ___ ___ ___ ___ ___ ___ ___ ___
CTG GGA TTG TCT GGA GCT GGA GAG GAG GGT GTC TTT GAC CTG CAG ATG TTC CTG
 L   G   L   S   G   A   G   E   E   G   V   F   D   L   Q   M   F   L 789              798              807              816              825              834
___ ___ ___ ___ ___ ___ ___ ___ ___ ___ ___ ___ ___ ___ ___ ___ ___ ___
GAG AAC ATG AAG GTG GAT TTC CTA CGC AGC CTT AAC CTC AGC GGC ATT CCC TCC
 E   N   M   K   V   D   F   L   R   S   L   N   L   S   G   I   P   S
```

Figure 1B

|     | 843 |     |     | 852 |     |     | 861 |     |     | 870 |     |     | 879 |     |     | 888 |     |
| --- | --- | --- | --- | --- | --- | --- | --- | --- | --- | --- | --- | --- | --- | --- | --- | --- | --- |
| CAG | GAC | AAA | ACC | AGA | GCG | GAG | CCA | CCC | CAG | TAC | ATG | ATC | GAC | TTG | TAC | AAC | AGA |
| Q   | D   | K   | T   | R   | A   | E   | P   | P   | Q   | Y   | M   | I   | D   | L   | Y   | N   | R   |

|     | 897 |     |     | 906 |     |     | 915 |     |     | 924 |     |     | 933 |     |     | 942 |     |
| --- | --- | --- | --- | --- | --- | --- | --- | --- | --- | --- | --- | --- | --- | --- | --- | --- | --- |
| TAC | ACA | ACG | GAC | AAA | TCG | TCT | ACG | CCT | GCC | TCC | AAC | ATC | GTG | CGG | AGC | TTC | AGC |
| Y   | T   | T   | D   | K   | S   | S   | T   | P   | A   | S   | N   | I   | V   | R   | S   | F   | S   |

|     | 951 |     |     | 960 |     |     | 969 |     |     | 978 |     |     | 987 |     |     | 996 |     |
| --- | --- | --- | --- | --- | --- | --- | --- | --- | --- | --- | --- | --- | --- | --- | --- | --- | --- |
| GTG | GAA | GAT | GCT | ATA | TCG | ACA | GCT | GCC | ACG | GAG | GAC | TTC | CCC | TTT | CAG | AAG | CAC |
| V   | E   | D   | A   | I   | S   | T   | A   | A   | T   | E   | D   | F   | P   | F   | Q   | K   | H   |

|     | 1005 |     |     | 1014 |     |     | 1023 |     |     | 1032 |     |     | 1041 |     |     | 1050 |     |
| --- | --- | --- | --- | --- | --- | --- | --- | --- | --- | --- | --- | --- | --- | --- | --- | --- | --- |
| ATC | CTG | ATC | TTC | AAC | ATC | TCC | ATC | CCG | AGG | CAC | GAG | CAG | ATC | ACC | AGG | GCT | GAG |
| I   | L   | I   | F   | N   | I   | S   | I   | P   | R   | H   | E   | Q   | I   | T   | R   | A   | E   |

|     | 1059 |     |     | 1068 |     |     | 1077 |     |     | 1086 |     |     | 1095 |     |     | 1104 |     |
| --- | --- | --- | --- | --- | --- | --- | --- | --- | --- | --- | --- | --- | --- | --- | --- | --- | --- |
| CTC | CGA | CTC | TAT | GTC | TCC | TGC | CAA | AAT | GAT | GTG | GAC | TCC | ACT | CAT | GGG | CTG | GAA |
| L   | R   | L   | Y   | V   | S   | C   | Q   | N   | D   | V   | D   | S   | T   | H   | G   | L   | E   |

|     | 1113 |     |     | 1122 |     |     | 1131 |     |     | 1140 |     |     | 1149 |     |     | 1158 |     |
| --- | --- | --- | --- | --- | --- | --- | --- | --- | --- | --- | --- | --- | --- | --- | --- | --- | --- |
| GGA | AGC | ATG | GTC | GTT | TAT | GAT | GTT | CTG | GAG | GAC | AGT | GAG | ACT | TGG | GAC | CAG | GCC |
| G   | S   | M   | V   | V   | Y   | D   | V   | L   | E   | D   | S   | E   | T   | W   | D   | Q   | A   |

|     | 1167 |     |     | 1176 |     |     | 1185 |     |     | 1194 |     |     | 1203 |     |     | 1212 |     |
| --- | --- | --- | --- | --- | --- | --- | --- | --- | --- | --- | --- | --- | --- | --- | --- | --- | --- |
| ACG | GGG | ACC | AAG | ACC | TTC | TTG | GTA | TCC | CAG | GAC | ATT | CGG | GAC | GAA | GGA | TGG | GAG |
| T   | G   | T   | K   | T   | F   | L   | V   | S   | Q   | D   | I   | R   | D   | E   | G   | W   | E   |

|     | 1221 |     |     | 1230 |     |     | 1239 |     |     | 1248 |     |     | 1257 |     |     | 1266 |     |
| --- | --- | --- | --- | --- | --- | --- | --- | --- | --- | --- | --- | --- | --- | --- | --- | --- | --- |
| ACT | TTA | GAA | GTA | TCG | AGT | GCC | GTG | AAG | CGG | TGG | GTC | AGG | GCA | GAC | TCC | ACA | ACA |
| T   | L   | E   | V   | S   | S   | A   | V   | K   | R   | W   | V   | R   | A   | D   | S   | T   | T   |

|     | 1275 |     |     | 1284 |     |     | 1293 |     |     | 1302 |     |     | 1311 |     |     | 1320 |     |
| --- | --- | --- | --- | --- | --- | --- | --- | --- | --- | --- | --- | --- | --- | --- | --- | --- | --- |
| AAC | AAA | AAT | AAG | CTC | GAG | GTG | ACA | GTG | CAG | AGC | CAC | AGG | GAG | AGC | TGT | GAC | ACA |
| N   | K   | N   | K   | L   | E   | V   | T   | V   | Q   | S   | H   | R   | E   | S   | C   | D   | T   |

|     | 1329 |     |     | 1338 |     |     | 1347 |     |     | 1356 |     |     | 1365 |     |     | 1374 |     |
| --- | --- | --- | --- | --- | --- | --- | --- | --- | --- | --- | --- | --- | --- | --- | --- | --- | --- |
| CTG | GAC | ATC | AGT | GTC | CCT | CCA | GGT | TCC | AAA | AAC | CTG | CCC | TTC | TTT | GTT | GTC | TTC |
| L   | D   | I   | S   | V   | P   | P   | G   | S   | K   | N   | L   | P   | F   | F   | V   | V   | F   |

Figure 1C

```
    1383            1392            1401            1410            1419            1428
    TCC AAT GAC CGC AGC AAT GGG ACC AAG GAG ACC AGA CTG GAG CTG AAG GAG ATG
     S   N   D   R   S   N   G   T   K   E   T   R   L   E   L   K   E   M 1437            1446            1455            1464            1473            1482
    ATC GGC CAT GAG CAG GAG ACC ATG CTT GTG AAG ACA GCC AAA AAT GCT TAC CAG
     I   G   H   E   Q   E   T   M   L   V   K   T   A   K   N   A   Y   Q 1491            1500            1509            1518            1527            1536
    GTG GCA GGT GAG AGC CAA GAG GAG GAG GGT CTA GAT GGA TAC ACA GCT GTG GGA
     V   A   G   E   S   Q   E   E   E   G   L   D   G   Y   T   A   V   G 1545            1554            1563            1572            1581            1590
    CCA CTT TTA GCT AGA AGG AAG AGG AGC ACC GGA GCC AGC AGC CAC TGC CAG AAG
     P   L   L   A   R   R   K   R   S   T   G   A   S   S   H   C   Q   K
                                            (319)                   (326)

1599            1608            1617            1626            1635            1644
    ACT TCT CTC AGG GTG AAC TTT GAG GAC ATC GGC TGG GAC AGC TGG ATC ATT GCA
     T   S   L   R   V   N   F   E   D   I   G   W   D   S   W   I   I   A 1653            1662            1671            1680            1689            1698
    CCC AAG GAA TAT GAC GCC TAT GAG TGT AAA GGG GGT TGC TTC TTC CCA TTG GCT
     P   K   E   Y   D   A   Y   E   C   K . G   G   C   F   F   P   L   A 1707            1716            1725            1734            1743            1752
    GAT GAC GTG ACA CCC ACC AAA CAT GCC ATC GTG CAG ACC CTG GTG CAT CTC GAG
     D   D   V   T   P   T   K   H   A   I   V   Q   T   L   V   H   L   E 1761            1770            1779            1788            1797            1806
    TTC CCC ACA AAG GTG GGC AAA GCC TGC TGC GTT CCC ACC AAA CTG AGT CCC ATC
     F   P   T   K   V   G   K   A   C   C   V   P   T   K   L   S   P   I 1815            1824            1833            1842            1851            1860
    TCC ATC CTC TAC AAG GAT GAC ATG GGG GTG CCA ACC CTC AAG TAC CAC TAT GAG
     S   I   L   Y   K   D   D   M   G   V   P   T   L   K   Y   H   Y   E 1869            1878            1887                    1903            1913    1923
    GGG ATG AGT GTG GCT GAG TGT GGG TGT AGG TAGTCCCTGC AGCCACCCAG GGTGGGGATA
     G   M   S   V   A   E   C   G   C   R
                                        (428)
```

Figure 1D

```
         1933       1943       1953       1963       1973       1983       1993
   CAGGACATGG AAGAGGTTCT GGTACGGTCC TGCATCCTCC TGCGCATGGT ATGCCTAAGT TGATCAGAAA
         2003       2013       2023       2033       2043       2053       2063
   CCATCCTTGA GAAGAAAAGG AGTTAGTTGC CCTTCTTGTG TCTGGTGGGT CCCTCTGCTG AAGTGACAAT
         2073       2083       2093       2103       2113       2123       2133
   GACTGGGGTA TGCGGGCCTG TGGGCAGAGC AGGAGACCCT GGAAGGGTTA GTGGGTAGAA AGATGTCAAA
         2143       2153       2163       2173       2183       2193       2203
   AAGGAAGCTG TGGGTAGATG ACCTGCACTC CAGTGATTAG AAGTCCAGCC TTACCTGTGA GAGAGCTCCT
         2213       2223       2233       2243       2253       2263       2273
   GGCATCTAAG AGAACTCTGC TTCCTCATCA TCCCCACCGA CTTGTTCTTC CTTGGGAGTG TGTCCTCAGG
         2283       2293       2303       2313       2323       2333       2343
   GAGAACAGCA TTGCTGTTCC TGTGCCTCAA GCTCCCAGCT GACTCTCCTG TGGCTCATAG GACTGAATGG
         2353       2363       2373       2383       2393       2403       2413
   GGTGAGGAAG AGCCTGATGC CCTCTGGCAA TCAGAGCCCG AAGGACTTCA AAACATCTGG ACAACTCTCA
         2423       2433       2443
    TTGACTGATG CTCCAACATA ATTTTTAAAA AGAG
```

Figure 2

```
         10         20         30         40         50         60         70
CTCTAGAGGG CAGAGGAGGA GGGAGGGAGG GAAGGAGCGC GGAGCCCGGC CCGGAAGCTA GGTGAGTGTG 80         90        100        110        120        130        140
GCATCCGAGC TGAGGGACGC GAGCCTGAGA CGCCGCTGCT GCTCCGGCTG AGTATCTAGC TTGTCTCCCC 150        160        170        180        190        200        210
GATGGGATTC CCGTCCAAGC TATCTCGAGC CTGCAGCGCC ACAGTCCCCG GCCCTCGCCC AGGTTCACTG 220        230        240        250        260        270        280
CAACCGTTCA GAGGTCCCCA GGAGCTGCTG CTGGCGAGCC CGCTACTGCA GGGACCTATG GAGCCATTCC 290        300        310        320        330        340        350
GTAGTGCCAT CCCGAGCAAC GCACTGCTGC AGCTTCCCTG AGCCTTTCCA GCAAGTTTGT TCAAGATTGG 360        370        380        390        400       (1)
CTGTCAAGAA TCATGGACTG TTATTATATG CCTTGTTTTC TGTCAAGACA CC ATG ATT CCT
                                                           MET Ile Pro
```

```
        417                       432                       447                       462
GGT AAC CGA ATG CTG ATG GTC GTT TTA TTA TGC CAA GTC CTG CTA GGA GGC GCG
Gly Asn Arg MET Leu MET Val Val Leu Leu Cys Gln Val Leu Leu Gly Gly Ala 477                       492                       507
AGC CAT GCT AGT TTG ATA CCT GAG ACG GGG AAG AAA AAA GTC GCC GAG ATT CAG
Ser His Ala Ser Leu Ile Pro Glu Thr Gly Lys Lys Lys Val Ala Glu Ile Gln 522                       537                       552                       567
GGC CAC GCG GGA GGA CGC CGC TCA GGG CAG AGC CAT GAG CTC CTG CGG GAC TTC
Gly His Ala Gly Gly Arg Arg Ser Gly Gln Ser His Glu Leu Leu Arg Asp Phe 582                       597                       612                       627
GAG GCG ACA CTT CTG CAG ATG TTT GGG CTG CGC CGC CGC CCG CAG CCT AGC AAG
Glu Ala Thr Leu Leu Gln MET Phe Gly Leu Arg Arg Arg Pro Gln Pro Ser Lys 642                       657                       672
AGT GCC GTC ATT CCG GAC TAC ATG CGG GAT CTT TAC CGG CTT CAG TCT GGG GAG
Ser Ala Val Ile Pro Asp Tyr MET Arg Asp Leu Tyr Arg Leu Gln Ser Gly Glu 687                       702                       717                       732
GAG GAG GAA GAG CAG ATC CAC AGC ACT GGT CTT GAG TAT CCT GAG CGC CCG GCC
Glu Glu Glu Glu Gln Ile His Ser Thr Gly Leu Glu Tyr Pro Glu Arg Pro Ala 747                       762                       777
AGC CGG GCC AAC ACC GTG AGG AGC TTC CAC CAC GAA GAA CAT CTG GAG AAC ATC
Ser Arg Ala Asn Thr Val Arg Ser Phe His His Glu Glu His Leu Glu Asn Ile 792                       807                       822                       837
CCA GGG ACC AGT GAA AAC TCT GCT TTT CGT TTC CTC TTT AAC CTC AGC AGC ATC
Pro Gly Thr Ser Glu Asn Ser Ala Phe Arg Phe Leu Phe Asn Leu Ser Ser Ile
```

Figure 2A

```
      852                    867                    882                     897
CCT GAG AAC GAG GTG ATC TCC TCT GCA GAG CTT CGG CTC TTC CGG GAG CAG GTG
Pro Glu Asn Glu Val Ile Ser Ser Ala Glu Leu Arg Leu Phe Arg Glu Gln Val 912                    927                    942
GAC CAG GGC CCT GAT TGG GAA AGG GGC TTC CAC CGT ATA AAC ATT TAT GAG GTT
Asp Gln Gly Pro Asp Trp Glu Arg Gly Phe His Arg Ile Asn Ile Tyr Glu Val 957                    972                    987                   1002
ATG AAG CCC CCA GCA GAA GTG GTG CCT GGG CAC CTC ATC ACA CGA CTA CTG GAC
MET Lys Pro Pro Ala Glu Val Val Pro Gly His Leu Ile Thr Arg Leu Leu Asp 1017                   1032                   1047
ACG AGA CTG GTC CAC CAC AAT GTG ACA CGG TGG GAA ACT TTT GAT GTG AGC CCT
Thr Arg Leu Val His His Asn Val Thr Arg Trp Glu Thr Phe Asp Val Ser Pro 1062                   1077                   1092                   1107
GCG GTC CTT CGC TGG ACC CGG GAG AAG CAG CCA AAC TAT GGG CTA GCC ATT GAG
Ala Val Leu Arg Trp Thr Arg Glu Lys Gln Pro Asn Tyr Gly Leu Ala Ile Glu 1122                   1137                   1152                  1167
GTG ACT CAC CTC CAT CAG ACT CGG ACC CAC CAG GGC CAG CAT GTC AGG ATT AGC
Val Thr His Leu His Gln Thr Arg Thr His Gln Gly Gln His Val Arg Ile Ser 1182                   1197                   1212
CGA TCG TTA CCT CAA GGG AGT GGG AAT TGG GCC CAG CTC CGG CCC CTC CTG GTC
Arg Ser Leu Pro Gln Gly Ser Gly Asn Trp Ala Gln Leu Arg Pro Leu Leu Val 1227                   1242                   1257                  1272
ACC TTT GGC CAT GAT GGC CGG GGC CAT GCC TTG ACC CGA CGC CGG AGG GCC AAG
Thr Phe Gly His Asp Gly Arg Gly His Ala Leu Thr Arg Arg Arg Arg Ala Lys 1287                   1302                   1317
CGT AGC CCT AAG CAT CAC TCA CAG CGG GCC AGG AAG AAG AAT AAG AAC TGC CGG
Arg Ser Pro Lys His His Ser Gln Arg Ala Arg Lys Lys Asn Lys Asn Cys Arg

1332(311)              1347                   1362                   1377
CGC CAC TCG CTC TAT GTG GAC TTC AGC GAT GTG GGC TGG AAT GAC TGG ATT GTG
Arg His Ser Leu Tyr Val Asp Phe Ser Asp Val Gly Trp Asn Asp Trp Ile Val 1392                   1407                   1422                  1437
GCC CCA CCA GGC TAC CAG GCC TTC TAC TGC CAT GGG GAC TGC CCC TTT CCA CTG
Ala Pro Pro Gly Tyr Gln Ala Phe Tyr Cys His Gly Asp Cys Pro Phe Pro Leu 1452                   1467                   1482
GCT GAC CAC CTC AAC TCA ACC AAC CAT GCC ATT GTG CAG ACC CTG GTC AAT TCT
Ala Asp His Leu Asn Ser Thr Asn His Ala Ile Val Gln Thr Leu Val Asn Ser 1497                   1512                   1527                   1542
GTC AAT TCC AGT ATC CCC AAA GCC TGT TGT GTG CCC ACT GAA CTG AGT GCC ATC
Val Asn Ser Ser Ile Pro Lys Ala Cys Cys Val Pro Thr Glu Leu Ser Ala Ile
```

Figure 2B

```
           1557                      1572                    1587
TCC ATG CTG TAC CTG GAT GAG TAT GAT AAG GTG GTA CTG AAA AAT TAT CAG GAG
Ser MET Leu Tyr Leu Asp Glu Tyr Asp Lys Val Val Leu Lys Asn Tyr Gln Glu 1602                1617        (408)   1636         1646         1656
ATG GTA GTA GAG GGA TGT GGG TGC CGC TGAGATCAGG CAGTCCTTGA GGATAGACAG
MET Val Val Glu Gly Cys Gly Cys Arg 1666       1676       1686       1696       1706       1716       1726
ATATACACAC CACACACACA CACCACATAC ACCACACACA CACGTTCCCA TCCACTCACC CACACACTAC 1736       1746       1756       1766       1776       1786       1796
ACAGACTGCT TCCTTATAGC TGGACTTTTA TTTAAAAAAA AAAAAAAAAA AATGGAAAAA ATCCCTAAAC 1806       1816       1826       1836       1846       1856       1866
ATTCACCTTG ACCTTATTTA TGACTTTACG TGCAAATGTT TTGACCATAT TGATCATATA TTTTGACAAA 1876       1886       1896       1906       1916       1926       1936
ATATATTTAT AACTACGTAT TAAAAGAAAA AAATAAAATG AGTCATTATT TTAAAAAAAA AAAAAAAACT

1946
CTAGAGTCGA CGGAATTC
```

Figure 3

```
TGA ACA AGA GAG TGC TCA AGA AGC TGT CCA AGG ACG GCT CCA CAG AGG        48
 *  Thr Arg Glu Cys Ser Arg Ser Cys Pro Arg Thr Ala Pro Gln Arg
-41 -40             -35             -30

CAG GTG AGA GCA GTC ACG AGG AGG ACA CGG ATG GCG CAC GTG GCT GCG        96
Gln Val Arg Ala Val Thr Arg Arg Thr Arg Met Ala His Val Ala Ala
-25             -20             -15             -10

GGG TCG ACT TTA GCC AGG CGG AAA AGG AGC GCC GGG GCT GGC AGC CAC       144
Gly Ser Thr Leu Ala Arg Arg Lys Arg Ser Ala Gly Ala Gly Ser His
             -5              1               5

TGT CAA AAG ACC TCC CTG CGG GTA AAC TTC GAG GAC ATC GGC TGG GAC       192
Cys Gln Lys Thr Ser Leu Arg Val Asn Phe Glu Asp Ile Gly Trp Asp
         10              15              20

AGC TGG ATC ATT GCA CCC AAG GAG TAT GAA GCC TAC GAG TGT AAG GGC       240
Ser Trp Ile Ile Ala Pro Lys Glu Tyr Glu Ala Tyr Glu Cys Lys Gly
     25              30              35

GGC TGC TTC TTC CCC TTG GCT GAC GAT GTG ACG CCG ACG AAA CAC GCT       288
Gly Cys Phe Phe Pro Leu Ala Asp Asp Val Thr Pro Thr Lys His Ala
 40              45              50              55

ATC GTG CAG ACC CTG GTG CAT CTC AAG TTC CCC ACA AAG GTG GGC AAG       336
Ile Val Gln Thr Leu Val His Leu Lys Phe Pro Thr Lys Val Gly Lys
             60              65              70

GCC TGC TGT GTG CCC ACC AAA CTG AGC CCC ATC TCC GTC CTC TAC AAG       384
Ala Cys Cys Val Pro Thr Lys Leu Ser Pro Ile Ser Val Leu Tyr Lys
         75              80              85

GAT GAC ATG GGG GTG CCC ACC CTC AAG TAC CAT TAC GAG GGC ATG AGC       432
Asp Asp Met Gly Val Pro Thr Leu Lys Tyr His Tyr Glu Gly Met Ser
     90              95             100

GTG GCA GAG TGT GGG TGC AGG TAGTATCTGC CTGCGGG                        470
Val Ala Glu Cys Gly Cys Arg
105             110
```

BONE MORPHOGENETIC PROTEIN-9 COMPOSITIONS

CROSS REFERENCE TO RELATED APPLICATIONS

This application is a national stage of PCT/US92/05374, filed Jun. 25, 1992, which is a continuation in-part of U.S. Ser. No. 07/720,590 filed Jun. 25, 1991, now abandoned.

The present invention relates to a novel family of purified proteins designated BMP-9 proteins and processes for obtaining them. These proteins may be used to induce bone and/or cartilage formation and in wound healing and tissue repair.

The marine MBP-9 DNA sequence (SEQ ID NO: 1) and amino acid sequence (SEQ ID NO: 2) are set forth in FIG. 1. Human BMP-9 sequence is set forth in FIG. 3 (SEQ ID NO: 8 and SEQ ID NO: 9). It is contemplated that BMP-9 proteins are capable of inducing the formation of cartilage and/or bone. BMP-9 proteins may be further characterized by the ability to demonstrate cartilage and/or bone formation activity in the rat bone formation assay described below.

Murine BMP-9 is characterized by comprising amino acid #319 to #428 of FIG. (SEQ ID NO: 2 amino acid #1-110). Murine BMP-9 may be produced by culturing a cell transformed with a DNA sequence comprising nucleotide #610 to nucleotide #1893 as shown in FIG. 1 (SEQ ID NO: 1) and recovering and purifying from the culture medium a protein characterized by the amino acid sequence comprising amino acid #319 to #428 as shown in FIG. 1 (SEQ ID NO: 2) substantially free from other porteinanceous materials with which it is co-produced.

Human BMP-9 is expected to be homologous to murine BMP-9 and is characterized by comprising amino acid #1 (Ser, Ala, Gly) to #110 of FIG. 3 (SEQ ID NO: 9) (Arg). The invention includes methods for obtaining the DNA sequences encoding human BMP-9. This method entails utilizing the murine BMP-9 nucleotide sequence or portions thereof to design probes to screen libraries for the human gene or fragments thereof using standard techniques. Human BMP-9 may be produced by culturing a cell transformed with the BMP-9 DNA sequence and recovering and purifying 8MP-9 from the culture medium. The expressed protein is isolated, recovered, and purified from the culture medium. The parodied expressed protein is substantially free from other proteinaceous materials with which it is co-produced, as well as from other contaminants the recovered purified protein is contemplated to exhibit cartilage and/or bone formation activity. The proteins of the invention may be further characterized by the ability to demonstrate cartilage and/or bone formation activity in the rate bone formations assay described below.

Human BMP-9 maybe produced by culturing a cell transformed with a DNA sequence comprising nucleotide #124 to #453 as shown in SEQ ID NO: 8 and recovering and purifying from the culture medium a protein characterized by the amino acid sequence of SEQ ID NO: 9 from amino acid #1 to amino acid #110 substantially free from other proteinaceous materials with which it is co-produced.

Another aspect of the invention provides pharmaceutical compositions containing a therapeutically effective amount of a BMP-9 protein in a pharmaceutically acceptable vehicle or carrier. BMP-9 compositions of the invention may be used in the formation of cartilage. These compositions may further be utilized for the formation of bone. BMP-9 compositions may also be used for wound heading and tissue repair. Compositions of the invention may further include at least one other therapeutically useful agent such as the BMP proteins BMP-1, BMP-2, BMP-3, BMP-4, BMP-5, BMP-6, and BMP-7 disclosed for instance in PCT publications WO88/00205, WO89/10409, and WO90/11366, and BMP-8, disclosed in U.S. application Ser. No. 07/641,204 filed Jan. 15, 1991, Ser. No. 07/525,357 filed May 16, 1990, and Ser. No. 07/800,364 filed Nov. 20, 1991.

The compositions of the invention may comprise, in addition to a BMP-9 protein, other therapeutically useful agents including growth factors such as epidermal growth factor (EGF), fibroblast growth factor (FGF), transforming growth factor (TGF-$\alpha$ and TGF-$\beta$), and insulin-like growth factor (IGF). The compositions may also include an appropriate matrix for instance, for supporting the composition and providing a surface for bone and/or cartilage growth. The matrix may provide slow release of the osteoinductive protein and/or the appropriate environment for presentation thereof.

The BMP-9 compositions may be employed in methods for treating a number of bone and/or cartilage defects, periodontal disease and various types of wounds. These methods, according to the invention, entail administering to a patient needing such bone and/or cartilage formation wound healing or tissue repair, an effective amount of a BMP-9 protein. These methods may also entail the administration of a protein of the invention in conjunction with at least one of the novel BMP proteins disclosed in the co-owned applications described above. In addition, these methods may also include the administration of a BMP-9 protein with other growth factors including EGF, FGF, TGF-$\alpha$, TGF-$\beta$, and IGF.

Still a further aspect of the invention are DNA sequences coding for expression of a BMP-9, protein. Such sequences include the sequence of nucleotides in a 5' to 3' direction illustrated in FIG. 1 (SEQ ID NO: 1) and FIG. 3 (SEQ ID NO: 8) or DNA sequences which hybridize under stringent conditions with the DNA sequences of FIG. 1 or 3 and encode a protein having the ability to induce the formation of cartilage and/or bone. Finally, allelic or other variations of the sequences of FIG. 1 or 3, whether such nucleotide changes result in changes in the peptide sequence or not, are also included in the present invention.

A further aspect of the invention includes vectors comprising a DNA sequence as described above in operative association with an expression control sequence thereof. These vectors may be employed in a novel process for producing a DMP-9 protein of the invention in which a cell line transformed with a DNA sequence encoding a BMP-9 protein in operative association with an expression control sequence therefor, is cultured in a suitable culture medium and a BMP-9 protein is recovered and purified therefrom. This process may employ a number of known cells both prokaryotic and eukaryotic as host cells for expression of the polypeptide.

Other aspects and advantages of the present invention will be apparent upon consideration of the following detailed description and preferred embodiments thereof.

BRIEF DESCRIPTION OF THE DRAWING

FIG. 1A, 1B, 1C and 1D comprises DNA sequence and derived amino acid sequence of murine BMP-9 from clone ML14a further described below SEQ. ID. NO: 1 and 2.

FIG. 2A and 2B comprises DNA sequence and derived amino acid sequence of human BMP-4 from lambda U2OS-3 ATCC #40342, SEQ ID NO:3 and 4.

FIG. 3 comprises DNA sequence and derived amino acid sequence of human BMP-9 from $\lambda$ FIX/H6111 ATCC #75252, SEQ ID NO: 8 and 9.

DETAILED DESCRIPTION OF THE INVENTION

The murine BMP-9 nucleotide sequence (SEQ ID NO: 1) and encoded amino acid sequence (SEQ ID NO: 2) are depicted in FIG. 1. Purified murine BMP-9 proteins of the present invention are produced by culturing a host cell transformed wth a DNA sequence comprising the DNA coding sequence of FIG. 1 (SE ID NO: 1) from nucleotide #610 to nucleotide #1893 and recovering and purifying from the culture medium a protein which contains the amino acid sequence or a substantially homologous sequence as represented by amino acid #319 to #428 of FIG. 1 (SEQ ID NO: 2). The BMP-9 proteins recovered from the culture medium are purified by isolating them from other proteinaceous materials from which they are co-produced and from other contaminants present.

Human BMP-9 nucleotide and amino acid sequence is depicted in SEQ ID NO: 8 and 9. Mature human BMP-9 is expected to comprise amino acid #1 (Ser, Ala, Gly) to #110 (Arg).

Human BMP-9 may be produced by culturing a cell transformed with a DNA sequence comprising nucleotide #124 to #453 as shown in SEQ ID NO: 8 and recovering and purifying from the culture medium a protein characterized by the amino acid sequence of SEQ ID NO: 9 from amino acid #1 to amino acid #110 substantially free from other proteinaceous materials with which it is co-produced.

BMP-9 proteins maybe characterized by the ability to induce the formation of cartilage. BMP-9 proteins may be further characterized by the ability to induce the formation of bone. BMP-9 proteins may be further characterized by the ability to demonstrate cartilage and/or bone formations activity in the rat bone formation assay described below.

The BMP-9 proteins provided herein also include factors encoded by the sequences similar to those of FIG. 1 and 3 (SEQ ID NO's: 1 and 8), but into which modifications are sequence which may result in amino acid changes in the polypeptide) or deliberately engineered. For example, synthetic polypeptides may wholly or partially duplicate continuous sequences of the amino acid residues of FIG. 1 of FIG. 3 (SEQ ID NO's: 2 and 9). These sequences, by virtue of sharing primary, secondary, or tertiary structural and conformational characteristics with bone growth factor polypeptides of FIG. 1 and FIG. 3 may possess bone growth factor biological properties in common therewith. Thus, they may be employed as biologically active substitutes for naturally-occurring BMP-9 and other BMP-9 polypeptides in therapeutic processes.

Other specific mutations of the sequences of BMP-9 proteins described herein involve modifications of glycosylation sites. These modifications may involve O-linked or N-linked glycosylation sites. For instance, the absence of glycoslyation or only partial glycosylation results from amino acid substitution or deletion at asparagine-linked glycosylation recognition sites. These asparagine-linked glycoslyation recognition sites comprise tripeptide sequence which are specifically recognized by appropriate cellular glycosylation enzymes. These tripeptide sequences are either asparagine-X-thronine or asparagine-X-serine, where X is usually any amino acid. A variety of amino acid substitutions or deletions at one or both of the first or third amino acid positions of a glycosylation recognition site (and/or amino acid deletion at the second position) results in non-glycosylation at the modified tripeptide sequence.

The present invention also encompasses the novel DNA sequences, free of association with DNA sequences encoding other proteinaceous materials, and coding on expression for DMP-9 proteins. These DNA sequences include those depicted in FIG. 1 or FIG. 3 (SEQ ID NO's: 1 and 8) in a 5' to 3' direction and those sequences which hybridize thereto under stringent hybridization conditions [see T. Maniatis et al., *Molecular Cloning (A Laboratory Manual)*, Cold Spring Harbor Laboratory (1982), pages 387 to 389] and encode a protein having cartilage and/or bone inducing activity.

Similarly, DNA sequences which code for BMP-9 proteins coded for by the sequences of FIG. 1 or FIG. 3, but which differ in codon sequence due to the degeneracies of the genetic code or allelic variations (naturally-occurring base changes in the species population which may or may not result in an amino acid change) also encode the novel factors described herein. Variations in the DNA sequences of FIG. 1 or FIG. 3 (SEQ ID NO: 1 and 8) which are caused by point mutations or by induced modifications (including insertion, deletion, and substitution) to enhance the activity, half-life or production of the polypeptides encoded are also encompassed in the invention.

Another aspect of the present invention provides a novel method for producing BMP-9 proteins. The method of the present invention involves culturing a suitable cell line, which has been transformed with a DNA sequence encoding a BMP-9 protein of the invention, under the control of known regulatory sequences. The transformed host cells are cultured and the BMP-9 proteins recovered and purified from the culture medium. The purified proteins are substantially free from other proteins with which they are co-produced as well as from other contaminants.

Suitable cells or cell lines may be mammalian cells, such as Chinese hamster ovary cells (CHO). The selection of suitable mammalian host cells and methods for transformation, culture, amplification, screening, product production and purification are known in the art. See, e.g., Gething and Sambrook, *Nature*, 293: 620–625 (1981), or alternatively, Kaufman et al., *Mol. Cell. Biol.*, 5(7): 1750–1759 (1985) or Howley et al., U.S. Pat. No. 4,419,446. Another suitable mammalian cell line, which is described in the accompanying examples, is the monkey COS-1 cell line. The mammalian cell CV-1 may also be suitable.

Bacterial cells may also be suitable hosts. For example, the various strains of *E. coli* (e.g., HB101, MC1061) are well-known as host cells in the field of biotechnology. Various strains of *B. subtilis, Pseudomonas*, other bacilli and the like may also be employed in this method.

Many strains of yeast cells known to those skilled in the art may also be available as host cells for expression of the polypeptides of the present invention. Additionally, where desired, insect cells may be utilized as host cells in the method of the present invention. See, e.g. Miller et al., *Genetic Engineering*, 8: 277–298 (Plenum Press 1986) and references cit therein.

Another aspect of the present invention provides vectors for use in the method of expression of these novel BMP-9 polypeptides. Preferably the vectors contain the full novel DNA sequences described above which encode the novel factors of the invention. Additionally the vectors also contain appropriate expression control sequences permitting expression of the BMP-9 protein sequences. Alternatively, vectors incorporating modified sequences as described above are also embodiments of the present invention. The vectors may be employed in the method of transforming cell lines and contain selected regulatory sequences in operative association with the DNA coding sequences of the invention which are capable of directing the replication and expression thereof in selected host cells. Regulatory sequences for such vectors are known to hose skilled in the art and may be selected depending upon the host cells. Such selection is routine and does not form part of the present invention.

A protein of the present invention, which induces cartilage and/or bone formation in circumstances where bone is not normally formed, has application in the healing of bone fractures and cartilage defects in humans and other animals. Such a preparation employing a BMP-9 protein may have prophylactic use in closed as well as open fracture reduction and also in the improved fixation of artificial joints. De novo bone formation induced by an osteogenic agent contributes to the repair of congenital, trauma induced, or oncologic resection induced craniofacial defects, and also is useful in cosmetic plastic surgery. A BMP-9 protein may be used in the treatment of periodontal disease, and in other tooth repair processes. Such agents may provide an environment to attract bone-forming cells, stimulate growth of bone-forming cells or induce differentiation of progenitors of bone-forming cells, BMP-9 polypeptides of the invention may also be useful in the treatment of osteoporosis. A variety of osteogenic, cartilage-inducing and bone inducing factors have been described. See, e.g. European patent applications 148,155 and 169,016 for discussions thereof.

The proteins of the invention may also be used in wound healing and related tissue repair. The types of wounds include, but are not limited to burns, incisions and ulcers. (See, e.g. PCT Publication WO80/01106 for discussion of wound healing and related tissue repair).

It is further contemplated that proteins of the invention may increase neuronal survival and therefore be useful in transplantation and treatment of conditions exhibiting a decrease in neuronal survival.

A further aspect of the invention is a therapeutic method and composition for repairing fractures and other conditions related to cartilage and/or bone defects or periodontal diseases. The invention further comprises therapeutic methods and compositions for wound healing and tissue repair. Such compositions comprise a therapeutically effective amount of at least one of the BMP-9 proteins of the invention in admixture with a pharmaceutically acceptable vehicle, carrier or matrix.

It is expected that the proteins of the invention may act in concert with or perhaps synergistically with other related proteins and growth factors. Further therapeutic methods and compositions of the invention therefore comprise a therapeutic amount of at least one BMP-9 protein of the invention with a therapeutic amount of at least one of the other BMP proteins disclosed in co-owned applications described above. Such combinations may comprise separate molecules of the BMP proteins or heteromolecules comprised of different BMP moieties. For example, a method and composition of the invention may comprise a disulfide linked diner comprising a BMP-9 protein subunit and a subunit from one of the "BMP" proteins described above. A further embodiment may comprise a heterodimer of BMP-9 moieties. Further, BMP-9 proteins may be combined with other agents beneficial to the treatment of the bone and/or cartilage defect, wound, or tissue in question. These agents include various growth factors such as epidermal growth factor (EGF), platelet derived growth factor (PDGF), transforming growth factors (TGF-α and TGF-β), and insulin-like growth factor (IGF).

The preparation and formulation of such physiologically acceptable protein compositions, having due regard to pH, isotonicity, stability and the like, is within the skill of the art. The therapeutic compositions are also presently valuable for veterinary applications due to the lack of species specificity in BMP proteins. Particularly domestic animals and thoroughbred horses in addition to humans are desired patients for such treatment with BMP-9 of the present invention.

The therapeutic method includes administering the composition topically, systemically, or locally as an implant or derive. When administered, the therapeutic composition for use in this invention is, of course, in a pyrogen-free, physiologically acceptable form. Further, the composition may desirably be encapsulated or injected in a viscous form for delivery to the site of bone, cartilage or tissue damage. Topical administration may be suitable for wound healing and tissue repair. Therapeutically useful agents other than the BMP-9 proteins which may also optionally be included in the composition as described above, may alternatively or additionally, be administered simultaneously or sequentially with the BMP composition in the methods of the invention.

Preferably for bone and/or cartilage formation, the composition would include a matrix capable of delivering BMP-9 or other BMP proteins to the site of bone and/or cartilage damage, providing a structure for the developing bone and cartilage and optimally capable of being resorbed into the body. The matrix may provide slow release of BMP-9 and/or the appropriate environment for presentation thereof. Such matrices may be formed of materials presently in use for other implanted medical applications.

The choice of matrix material is based on biocompatibility, biodegradability, mechanical properties, cosmetic appearance and interface properties. The particular application of the BMP-9 compositions will define the appropriate formulation. Potential matrices for the compositions may be biodegradable and chemically defined calcium sulfate, tricalciumphosphate, hydroxyapatite, polylactic acid and polyanhydrides. Other potential materials are biodegradable and biologically well defined, such as bone or dermal collagen. Further matrices are comprised of pure proteins or extracellular matrix components. Other potential matrices are nonbiodegradable and chemically defined, such as sintered hydroxyapatite, bioglass, aluminates, or other ceramics. Matrices may be comprised of combinations of any of the above mentioned types of material, such as polylactic acid and hydroxyapatite or collagen and tricalciumphosphate. The bioceramics may be altered in composition, such as in calcium-aluminate-phosphate and processing to alter pore size, particle size, particle shape, and biodegradability.

The dosage regimen will be determined by the attending physician considering various factors which modify the action of the BMP-9 protein, e.g. amount of bone weight desired to be formed, the site of bone damage, the condition of the damaged bone, the size of a wound, type of damaged tissue, the patient's age, sex, and diet, the severity of any infection, time of administration and other clinical factors. The dosage may vary with the type of matrix used in the reconstitution and the types of BMP proteins in the composition. The addition of other known growth factors, such as IGF I (insulin like growth factor I), to the final composition, may also effect the dosage. Progress can be monitored by periodic assessment of bone growth and/or repair, for example, x-rays, histomorphometric determinations and tetracycline labeling.

The following examples illustrate practice of the present invention in recovering and characterizing murine BMP-9 protein and employing it to recover the human and other BMP-9 proteins, obtaining the human proteins and expressing the proteins via recombinant techniques.

EXAMPLE I

Murine BMP-9

750,000 recombinants of a mouse liver cDNA library made in the vector lambdaZAP (Stratagene/Catalog #935302) are plated and duplicate nitrocellulose replicas made. A fragment of human BMP-4 DNA corresponding to nucleotides 1330–1627 of FIG. 2 (SEQ ID NO: 3) (the human BMP-4sequence) is $^{32}$P-labeled by the random priming procedure of Feinberg et al. [Anal. Biochem. 132: 6–13 (1983)] and hybridized to both sets of filters in SHB at 60° C. for 2 to 3 days. Both sets of filters are washed under reduced stringency conditions (4X SSC, 0.1% SDS at 60° C.). Many duplicate hybridizing recombinants of various intensities (approximately 92) are noted. 50 of the strongest hybridizing recombinant bacteriophage are plaque purified and their inserts are transferred to the plasmid Bluescript SK (+/−) according to the in vivo excision protocol described by the manufacturer (Stratagene). DNA sequence analysis of several recombinants indicate that they encode a protein homologous to ocher BMP proteins and other proteins in the TGF-β family. The DNA sequence and derived amino acid sequence of one recombinant, designated Mn14a, is set forth in FIG. 1. (SEQ ID NO: 1)

The nucleotide sequence of clone ML14a contains an open reading frame of 1284 bp, encoding a BMP-9 protein of 428 amino acids. The encoded 428 amino acid BMP-9 protein is contemplated to be the primary translation product as the coding sequence is preceded by 609 bp of 5' untranslated sequence with stop codons in all three reading frames. The 428 amino acid sequence predicts a BMP-9 protein with a molecular weight of 48,000 daltons.

Based on knowledge of other BMP proteins and other proteins within the TGF-β family, it is predicted that the precursor polypeptide would be cleaved at the multibasic sequence ARG-ARG-LYS-ARG amino acids #-4 to #-1 of SEQ ID NO:1 in agreement with a proposed consensus proteolytic processing sequence of ARG-X-X-ARG amino acids #-4 to #-1 of SEQ ID NO:1. Cleavage of the BMP-9 precursor polypeptide at this location would generate a 110 amino acid mature peptide beginning with the amino acid SER at position #319. of FIG. 1C and amino acid #1 of SEQ ID NO: 2. The processing of BMP-9 into the mature form is expected to involve dimerization and removal of the N-terminal region in a manner analogous to the processing of the related protein TGF-β [L. E. Gentry, et al., *Molec. & Cell. Biol.*, 8: 4162 (1988); R. Derynck, et al., *Nature* 316: 701 (1985)].

It is contemplated therefore that the mature active species of murine BMP-9 comprises a homodimer of 2 polypeptide subunits, each subunit comprising amino acids #319-#428 of FIG. 1C and amino acid #1 to #110 of SEQ ID NO: 2 with a predicted molecular weight of approximately 12,000 daltons. Further active species are contemplated comprising amino acids #326-#428 of FIG. 1C and amino acid #8-#110 of SEQ ID NO: 2 thereby including the first conserved cysteine residue. As with other members of the BMP and TGF-β family of proteins, the carboxy-terminal region of the BMP-9 protein exhibits greater sequence conservation than the more amino-terminal portion. The percent amino acid identity of the murine BMP-9 protein in the cysteine-rich C-terminal domain (amino acids #326-#428 of FIG. 1C and amino acid #8-#110 of SEQ ID NO: 2) to the corresponding region of other human BMP proteins and other proteins within the TGF-β family is as follows: BMP-2, 53%; BMP-3, 43%; BMP-4, 53%; BMP-5, 55%; BMP-6, 55%; BMP-7, 53%; Vgl, 50%; GDF-1, 43%; TGF-β1, 32%; TGF-β2, 34%; TGF-β3, 34%; inhibit β(B), 34%; and inhibin β(A), 42%.

EXAMPLE II

Human BMP-9

Murine and human osteoinductive factor genes are presumed to be significantly homologous, therefore the murine coding sequence or a portion thereof is used as a probe to screen a human genomic library or as a probe to identify a human cell line or tissue which synthesizes the analogous human cartilage and/or bone protein. A human genomic library (Toole et al., supra) may be screened with such a probe, and presumptive positives isolated and DNA sequence obtained. Evidence that this recombinant encodes a portion of the human BMP-9 relies of the murine/human protein and gene structure homologies.

Once a recombinant bacteriophage containing DNA encoding portion of the human cartilage and/or bone inductive factor molecule is obtained, the human coding sequence can be used as a probe to identify a human cell line or tissue which synthesizes BMP-9. Alternatively, the murine coding sequence can be used as a probe to identify such human cell line or tissue. Briefly described, RNA is extracted from a selected cell or tissue source and either electrophoresed on a formaldehyde agarose gel and transferred to nitrocellulose, or reacted with formaldehyde and spotted on nitrocellulose directly. The nitrocellulose is then hybridized to a probe derived from a coding sequence of the murine or human BMP-9. mRNA is selected by oligo (dT) cellulose chromatography and cDNA is synthesized and cloned in lambda gt10 or lambda ZAP by established techniques (Toole et al., spura).

Additional methods known to those skilled in the art may be used to isolate the human and other species' BMP-9 proteins of the invention.

A. Isolation of Human BMP-9 DNA

One million recombinants of a human genomic library constructed in the vector λFIX (Stratagene catalog #944201) are plated and duplicate nitrocellulose replicas made. Two oligonucleotides probes designed on the basis of nucleotides #1665-#1704 and #1837-#1876 of the sequence set forth in FIG. 1 (SEQ ID NO:1) are synthesized on an automated DNA synthesizer. The sequence of these two oligonucleotides in indicated below:

1: CTATGAGTGTAAAGGGGGTTGCTTCTTC-CCATTGGCTGAT (SEQ ID NO:10)

2: GTGCCAACCCTCAAGTACCACTAT-GAGGGGATGAGTGTGG (SEQ ID NO;11)

These two oligonucleotide probes are radioactively labelled with γ$^{32}$P-ATP and each is hybridized to one set of the duplicate nitrocellulose replicas in SHB at 65° C. and washed with 1X SSC, 0.1% SDS at 65° C. Three recombinants which hybridize to both oligonucleotide probes are noted. All three positively hybridizing recombinants are plaque purified, bacteriophage plate socks are prepared and bacteriophage DNA is isolated from each. The oligonucleotide hybridizing regions of one of these recombinants, designated HG111, is localized to a 1.2 kb Pst I/Xba I fragment. This fragment is subcloned into a plasmid vector (pGEM-3) and DNA sequence analysis is performed HG111 was deposited with the ATCC, 12301 Parklawn Drive, Rockville, Md. USA on Jun. 16, 1992 under the requirements of the Budapest Treaty and designated as ATCC #75252. This subclone is designated pGEM-111. A portion of the DNA sequence of clone pGEM-111 is set forth in FIG. 3 (SEQ ID NO:8/ HUMAN BMP-9 sequence). This sequence encodes the entire mature region of human BMP-9 and a portion of the propeptide. It should be noted that this sequence consists of preliminary data. Particularly, the propeptide region is subject to further analysis and characterization. For example, nucleotides #1 through #3 (TGA) encode a translation stop which may be incorrect due to the preliminary nature of the sequence. It is predicted that additional sequences present in both pGEM-111 (the 1.2 kb PstI/XbaI fragment of HG111 subcloned into pGEM) and HG111 encode additional amino acids of the human BMP-9 propeptide region. Based on knowledge of other BMPs and other proteins within the TGF-$\beta$ family, it is predicted that the precursor polypeptide would be cleaved at the multibasic sequence ARG-ARG-LYS-ARG (amino acids #-4 through #-1 of SEQUENCE ID NO:9) in agreement with a proposed consensus proteolytic processing sequence ARG-X-X-ARG amino acids #-4 to #1 to SEQ ID NO:1. Cleavage of the human BMP-9 precursor polypeptide at this location would generate a 110 amino acid mature peptide beginning with the amino acid SER at position #1 of SEQUENCE ID NO: 9 (encoded by nucleotides #124 through #126 of SEQUENCE ID NO:8). The processing of human BMP-9 into the mature form is expected to involve dimerization and removal of the N-terminal region in a manner analogous to the processing of the related protein TGF-$\beta$ [L. E. Gentry, et al., Molec. & Cell. Biol. 8: 4162 (1988); R. Derynck, et al., Nature 316: 701 (1985)].

It is contemplated therefore that the mature active species of human BMP-9 comprises a homodimer of two polypeptide subunits, each subunit comprising amino acids #1 through #110 of SEQUENCE. ID NO:9, with a predicted molecular weight of 12,000 daltons. Further active species are contemplated comprising amino acids #8 through #110 thereby including the first conserved cysteine residue. As with other members of the BMP and TGF-$\beta$ family of proteins, the carboxy-terminal portion of the human BMP-9 sequence exhibits greater sequence conservation than the amino terminal portion. the percent amino acid identity of the human BMP-9 protein in the cysteine-rich C-terminal domain (amino acids #8 through #110) to the corresponding region of other human BMP proteins and other proteins within the TGF-$\beta$ family is as follows: BMP-2, 52%; BMP-3, 40%; BMP-4, 52%; BMP-5, 55%; BMP-6, 55%; BMP-7, 53%; murine BMP-9, 97%; Vg1, 50%; GDF-1, 44%; TGF-$\beta$1, 32%; TGF-$\beta$2, 32%; TGF-$\beta$3; 32%; inhibin $\beta$ (B), 35%; and inhibin $\beta$ (A), 41%.

EXAMPLE III

Rosen Modified Sampath-Reddi Assay

A modified version of the rat bone formation assay described in Sampath and Reddi, Proc. Natl. Acad. Sci. U.S.A., 80: 6591–6595 (1983) is used to evaluate bone and/or cartilage activity of the BMP proteins. This modified assay is herein called the Rosen-modified Sampath-Reddi assay. The ethanol precipitation step of the Sampath-Reddi procedure is replaced by dialyzing (if the composition is a solution) or diafiltering (if the composition is a suspension) the fraction to be assayed against water. The solution or suspension is then redissolved in 1.1% TGA, and the resulting solution added to 20 mg of rat matrix. A mock rat matrix sample not treated with the protein serves as a control. This material is frozen and lyophilized and the resulting powder enclosed in #5 gelatin capsules. The capsules are implanted subcutaneously in the abdominal thoracic area of 21–49 day old male Long Evans rats. The implants are removed after 7–14 days. Half of each implant is used for alkaline phosphates analysis [See, A. H. Reddi et al., Proc. Natl. Acad. Sci., 69: 1601 (1972)].

The other half of each implant is fixed and processed for histological analysis. 1 $\mu$m glycolmethacrylate sections are stained with Von Kossa and acid fuschin to score the amount of induced bone and cartilage formation present in each implant. The terms +1 through +5 represents the area of each histological section of an implant occupied by new bone and/or cartilage cells and matrix. A score of +5 indicates that greater than 50% of the implant is new bone and/or cartilage produced as direct result of protein in the implant. A score of +4, +3, +2 and +1 would indicate that greater than 40%, 30%, 20% and 10% respectively of the implant contains new cartilage and/or bone. In a modified scoring method, three non-adjacent sections are evaluated from each implant and averaged. "+/–" indicates tentative identification of cartilage or bone; "+1" indicates >10% of each section being new cartilage or bone; "+2", >25%; "+3", >50%; "+4", –75%; "+5", >80%. A "–" indicates that the implant is not recovered.

It is contemplated that the dose response nature of the BMP-9 containing samples of the matrix samples will demonstrate that the amount of bone and/or cartilage formed increases with the amount of BMP-9 in the sample. It is contemplated that the control samples will not result in any bone and/or cartilage formation.

As with other cartilage and/or bone inductive proteins such as the above-mentioned "BMP" proteins, the bone and/or cartilage formed is expected to be physically confined to the space occupied by the matrix. Samples are also analyzed by SDS gel electrophoresis and isoelectric focusing followed by autoradiography. The activity is correlated with the protein bands and pI. To estimate the purity of the protein in a particular faction an extinction coefficient of 1 OD/mg-cm is used as an estimate for protein and the protein is run on SDS PAGE followed by silver staining or radio-iodination and autoradiography.

EXAMPLE IV

Expression of BMP-9

In order to produce murine, human or other mammalian BMP-9 proteins, the DNA encoding it is transferred into an appropriate expression vector and introduced into mammalian cells or other preferred eukaryotic or prokaryotic hosts by conventional genetic engineering techniques. The preferred expression system for biologically active recombinant human BMP-9 is contemplated to be stably transformed mammalian cells.

One skilled in the art can construct mammalian expression vectors by employing the sequence of FIG. 1 (SEQ ID NO: 1) or FIG. 3 (SEQ ID NO: 8), or other DNA sequences encoding BMP-9 proteins or other modified sequences and known vectors, such as pCD [Okayama et al., Mol. Cell Biol., 2: 161–170 (1982)], pJL3, pJL4 [Gough et al., EMBO J. 4: 645–653 (1985)] and pMT2 CXM.

The mammalian expression vector pMT2 CXM is a derivative of p91023 (b) (Wong et al., Science 228: 810–815, 1985) differing from the latter in that it contains the ampicillin resistance gene in place of the tetracycline resistance gene and further contains a XhoI site for insertion of cDNA clones. The functional elements of pMT2 CXM have been described (Kaufman R. J., 1985, Proc. Natl. Acad.

Sci. USA 82: 689–693) and include the adenovirus VA genes, the SV40 origin of replication including the 72 bp enhancer, the adenovirus major later promoter including a 5' splice site and the majority of the adenovirus tripartite leader sequence present on adenovirous late mRNAs, a 3' splice acceptor site, a DHFR insert, the SV40 early polyadenylation site (SV40), and pBR322 sequences needed for propagation in E. coli.

fragment. This fragment is digested with TaqI yielding an Eco RI-TaqI fragment of 508 bp which is purified by electrophoresis on low melting agarose gel. A 68 bp adapter and its complementary strand are synthesized with a 5'TaqI protruding end and a 3' XhoI protruding end which has the following sequence:

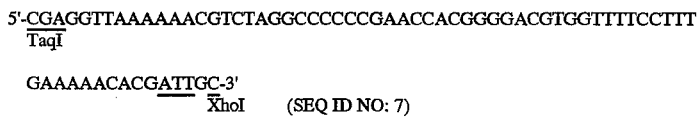

Plasmid pMT2 CXM is obtained by EcoRI digestion of pMT2-WVF, which has been deposited with the American Type Culture Collection (ATCC)., Rockville, Md. (USA) under accession number ATCC 67122. EcoRI digestion excises the cDNA insert present in pMT2-VWF, yielding pMT2 in linear form which can be ligated and used to transform E. coli HB 101 or DH-5 to ampicillin resistance. Plasmid pMT2 DNA can be prepared by conventional methods. pMT2 CXM is then constructed using loopout/in mutagenesis [Morinaga, et al., Biotechnology 84: 636 (1984). This removes bases 1075 to 1145 relative to the Hind III site near the SV40 origin of replication and enhancer sequences of pMT2. In addition it inserts the following sequence:

5' PO-CATGGGCAGCTCGAG-3' (SEQ ID NO: 5)

at nucleotide 1145. This sequence contains the recognition site for the restriction encodnuclease Xho I. A derivative of pMT2CXM, termed pMT23, contains recognition sites for the restriction endonucleases PstI, Eco RI, SalI and XhoI. Plasmid pMT2 CXM and pMT23 DNA may be prepared by conventional methods.

pEMC2B1 derived from pMT21 may also be suitable in practice of the invention. pMT21 is derived from pMT2 which is derived from pMT2-VWF. As described above EcoRI digestion excises the cDNA insert present in pMT-VWF, yielding pMT2 in linear from which can be ligated and used to transform E. Coli HB 101 or DH-5 to ampicillin resistance. Plasmid pMT2 DNA can be prepared by conventional methods.

pMT21 is derived from pMT2 through the following two modifications. First, 76 bp of the 5' untranslated region of the DHFR cDNA including a stretch of 19 G residues from G/C tailing for cDNA cloning is deleted. In this process, a XhoI site is inserted to obtain the following sequence immediately upstream from DHFR:

5'-CTGCAGGCGAGCCTGAATTCCTCGAGCCATCATG-3'
    PstI              Eco RI XhoI
(SEQ ID NO: 6)

Second, a unique ClaI site is introduced by digestion with EcoRV and XbaI, treatment with Klenow fragment of DNA polymerase I, and ligation to a ClaI linker (CATCGATG). This deletes a 250 bp segment from the adenovirus associated RNA (VAI) region but does not interfere with VAI RNA gene expression or function. pMT21 is digested with EcoRI and XhoI, and used to derive the vector pEMC2B1.

A portion of the EMCV leader is obtained from pMT2-ECAT1 [S. K. Jung, et al, J. Virol 63: 1651–1660.(1989)] by digestion with Eco RI and PstI, resulting in a 2752 bp This Sequence matches the EMC virus leader sequence from nucleotide 763to 827. It also changes the ATG at position 10 within the EMC virus leader to an ATT and is followed by a XhoI site. A three way ligation of the pMT21 Eco RI-XhoI fragment, the EMC virus EcoRI-TaqI fragment, and the 68 bp oligonucleotide adapter TaqI-XhoI adapter resulting in the vector pEMC2β1.

This vector contains the SV40 origin of replication and enhancer, the adenovirus major late promoter, a cDNA copy of the majority of the adenovirus tripartite leader sequence, a small hybrid intervening sequence, an SV40 polyadenylation signal and the adenovirus VA I gene, DHFR and β-lactamase markers and an EMC sequence; in appropriate relationships to direct the high level expression of the desired cDNA in mammalian cells.

The construction of vectors may involve modification of the BMP-9 DNA sequences. For instance, BMP-9 cDNA can be modified by removing the non-coding nucleotides on the 5' and 3' ends of the coding region. The deleted non-coding nucleotides may or may not be replaced by other sequences known to be beneficial for expression. These vectors are transformed into appropriate host cells for expression of BMP-9 proteins.

One skilled in the art can manipulate the sequences of FIG. 1 or FIG. 3 (SEQ ID NO: 1 and 8) by eliminating or replacing the mammalian regulatory sequences flanking the coding sequence with bacterial sequences to create bacterial vectors for intracellular or extracellular expression by bacterial cells. For example, the coding sequences could be further manipulated (e.g. ligated to other known linkers or modified by deleting non-coding sequences therefrom or altering nucleotides therein by other known techniques). The modified BMP-9 coding sequence could then be inserted into a known bacterial vector using procedures such as described in T. Taniguchi et al., Proc. Natl. Acad. Sci. USA, 77: 5230–5233 (1980). This exemplary bacterial Vector could then be transformed into bacterial host cells and a BMP-9 protein expressed thereby: For a strategy for producing extracellular expression of BMP-9 proteins in bacterial cells, see, e.g. European patent application EPA 177, 343.

Similar manipulations can be performed for the construction of an insect vector [See, e.g. procedures described in published European patent application 155,476] for expression in insect cells. A yeast vector could also be constructed employing yeast regulatory sequences for intracellular or extracellular expression of the factors of the present invention by yeast cells. [See, e.g., procedures described in published PCT application WO86/00639 and European patent application EPA 123,289].

A method for producing high levels of a BMP-9 protein of the invention in mammalian cells may involve the construction of cells containing multiple copies of the heterologous. BMP-9 gene. The heterologous gene is linked to an amplifiable marker, e.g. the dihydrofolate reductase (DHFR) gene for which cells containing increased gene copies can be selected for propagation in increasing concentrations of methotrexate (MTX) according to the procedures of Kaufman and Sharp, *J. Mol. Biol.*, 159: 601–629 (1982). This approach can be employed with a number of different cell types.

For example, a plasmid containing a DNA sequence for a BMP-9 of the invention in operative association with other plasmid sequences enabling expression thereof and the DHFR expression plasmid pAdA26SV(A)3 [Kaufman and sharp, *Mol. Cell. Biol.*, 2: 1304 (1982)] can be co-introduced into DHFR-deficient CHO cells, DUKX-BII, by various methods including calcium phosphate coprecipitation and transfection, electroporation or protoplast fusion. DHFR expressing transformants are selected for growth in alpha media with dialyzed fetal calf serum, and subsequently selected for amplification by growth in increasing concentrations Of MTX (e.g. sequential steps in 0.02, 0.2, 1.0 and 5 uM MTX) as described in Kaufman et al., *Mol Cell Biol.*, 5: 1750 (1983). Transformants are cloned, and biologically active BMP-9 expression is monitored by the Rosen-modified Sampath—Reddi rat bone formation assay described above in Example III. BMP-9 expression should increase with increasing levels of MTX resistance. BMP-9 polypeptides are characterized using standard techniques known in the art such as pulse labeling with [35S] methionine or cysteine and polyacrylamide gel electrophoresis. Similar procedures can be followed to produce other related BMP-9 proteins.

A. BMP-9 Vector construction

In order to produce human BMP-9 proteins of the invention DNA sequences encoding the mature region of the human BMP-9 protein may be joined to DNA sequences encoding the propeptide region of the murine BMP-9 protein. This murine/human hybrid DNA sequence is inserted into an appropriate expression vector and introduced into mammalian cells or other preferred eukaryotic or prokaryotic hosts by conventional genetic engineering techniques. The construction of this murine/human BMP-9 containing expression plasmid is described below. A derivative of the human BMP-9 sequence (SEQ ID NO:8) comprising the nucleotide sequence from nucleotide #105 to #470 is specifically amplified. The following oligonucleotides are utilized as primers to allow the amplification of nucleotides #105 to #470 of the human BMP-9 sequence (SEQ ID NO:8) from clone pGEM-111 described above.

3 ATCGGGCCCCTTTTAGCCAGGCGGAAAAGGAG (SEQ ID NO:12)

4 AGCGAATTCCCCGCAGGCAGATACTACCTG (SEQ ID NO:13)

This procedure generates the insertion of the nucleotide sequence ATCGGGCCCCT immediately preceeding nucleotide #105 and the insertion of the nucleotide sequence GAATTCGCT immediately following nucleotide #470. The addition of these sequences results in the creation of an Apa I and EcOR I restriction endonuclease site at the respective ends of the specifically amplified DNA fragment. The resulting 374 bp Apa I/EcoR I fragment is subcloned into the plasmid vector pGEM-7Zf(+) (Promega catalog#p2251) which has been digested with Apa I and EcoR I. The resulting clone is designated phBMP9mex-1.

The following oligonucleotides are designed on the basis of murine BMP-9 sequences (SEQ ID NO:1) and are modified to facilitate the construction of the murine/human expression plasmid referred to above:

5

GATTCCGTCGACCACCATGTCCCCTGGGGCCTGGTCTAGATGGATACACAGCTGTGGGGCC (SEQ ID NO: 14)

6 CCACAGCTGTGTATCCATCTAGACCAGGCCCCAGGGGACATGGTGGTCGACG (SEQ ID NO: 15)

These oligonucleotides contain complimentary sequences which upon addition to each other facilitate the annealing (base pairing) of the two individual sequences, resulting in the formation of a double stranded synthetic DNA linker (designated LINK-1) in a manner indicated below:

```
       1    5   10        20         30         40         50         60
       |    |   |         |          |          |          |          |
    #5GATTCCGTCGACCACCATGTCCCCTGGGGCCTGGTCTAGATGGATACACAGCTGTGGGGCC
         GCAGCTGGTGGTACAGGGGACCCCGGACCAGATCTACCTATGTGTCGACACC (SEQ ID NO: 16) #6
```

This DNA linker (LINK-1) contains recognition sequences of restriction endonucleases needed to facilitate subsequent manipulations required to construct the murine/human expression plasmid, as well as sequences required for maximal expression of heterologous sequences in mammalian cell expression systems. More specifically (referring to the sequence numbering of oligonucleotide #5/LINK-1): nucleotides #1-#11 comprise recognition sequences for the restriction endonucleases BamH I and Sal I, nucleotides #11-#15 allow for maximal expression of heterologous sequences in mammallian cell expression systems, nucleotides #16-#31 correspond to nucleotides #610-#625 of the murine BMP-9 sequence (SEQ ID NO:1), nucleotides #32-#33 are inserted to facilitate efficient restriction digestion of two adjacent restriction encodnuclease sites (Eco0109 I and Xba I), nucleotides #34-#60 correspond to nucleotides #1515-#1541 of the murine BMP-9 sequence (SEQ ID NO:1) except that nucleotide #58 of synthetic oligonucleotide #5 is a G rather than the A which appears at position #1539 of SEQ ID NO: 1 (This nucleotide conversion results in the creation of an Apa I restriction endonuclease recognition sequence, without altering the amino acid sequence it is intended to encode, to facilitate further manipulations of the murine/human hybrid expression plasmid. Link-1 (the double stranded product of the annealing of oligonucleotides #5 and #6) is subcloned into the plasmid vector pGEM-7Zf (+) which has been digested with the restriction endonucleases Apa I and BamH I. This results in a plasmid in which the sequences normally present between the Apa I and BamH I sites of the pGEM-7Zf(+) plasmid polylinker are replaced with the sequences of LINK-1 described above. The resulting plasmid clone is designated pBMP-9 link.

pBMP-9link is digested with the restriction endonucleases BamH I and Xba I resulting in the removal nucleotides #1-#34 of LINK-1 (refer to the numbering of oligo #5). Clone ML14a, which contains an insert comprising the sequence set forth in SEQ ID NO:1, is also digested with the restriction endonucleases BamH I and Xba I resulting in the removal of sequences comprising nucleotides #1-#1515 of SEQUENCE IN NO:1 (murine BMP-9). This BamH I/Xba I fragment of mouse BMP-9 is isolated from the remainder of the ML14a plasmid clone and subcloned into the BamH I/Xba I sites generated by the removal of the synthetic linker sequences described above. The resulting clone is designated p302.

The p302 clone is digested with the restriction endonuclease EcoO109 I resulting in the excision of nucleotides corresponding to nucleotides #621-#1515 of the murine BMP-9 sequence (SEQ ID No:1) and nucleotides #35-#59 of LINK-1 (SEQ ID NO:16) (refer to numbering of oligonucleotide #5). It should be noted that the Ape I restriction site created in LINK-1 by the A to G conversion described above is a subset of the recognition sequence of EcoO109 I, therefore digestion of p302 with EcoO109 I cleaves at the Ape I site as well as the naturally occuring murine EcoO109 I (location #619-#625 of SEQ ID NO:1) resulting in the excision of a 920 bp EcoO109 I/EeoC109 I (Ape I) fragment comprising the sequences described above. This 920 EcoO109 I/EcoO109 I (Ape I) fragment is isolated from the remainder of the p302 plasmid clone and subcloned into clone pBMP-9link which has been similarly digested with EcoO109 It should be noted that the nucleotides GG (#32-#33 of oligonucleotide #5) (SEQ ID NO:14) originally designed to facilitate a more complete digestion of the two adjacent restriction sites EcoO109 I and Xba I of LINK-1, which is now a part of pBMP-9link (described above), results in the creation of Dcm methylation recognition sequence. The restriction nucleuse EcoO109 I is sensitive to Dcm methylation and therefore cleavage of this sequence (nucleotides #25-#31 of oligoeucleotide #5/LINK-I) (SEQ ID NO:14/16) by the restriction endonuclease EcoO109 I is prevented at this site. Therefore the plasmid clone pBMP-9link is cleaved at the Ape I site but not at the EcoO109 I site upon digestion with the restriction endonuclease EcoO109 I as described above, preventing the intended removal of the sequences between the EcoO109 I and Xba I site of LINK-1 (#32-#55 defined by the numbering of oligonucleotide #5) (SEQ. ID NO:14). This results in the insertion of the 920 bp EcoO109 I/Apa I fragment at the EcoO109 I (Apa I) site of pBMP-9link. The resulting clone is designated p318.

Clone p318 is digested with the restriction endonucleases Sal I and Apa I, resulting in the excision of sequences comprising nucleotides #6-#56 of LINK-1 (SEQ ID NO:16) (refer to oligo #5 for location), nucleotides #621-#1515 of murine BMP-9 (SEQ ID NO:1), and nucleotides #35-#60 of LINK-1 (SEQ ID NO:16) (refer to oligo #5 for location). The resulting 972 bp Sal I/Apa I fragment described above is isolated from the remainder of the p318 plasmid clone and will be utilized in subsequent manipulations.

the clone pHBMP9mex-1 (described above), which contains DNA sequences which encode the entire mature region and portions of the propeptide of the human BMP-9 protein, is digested with the restriction endonucleases Apa I and EcoR I. This results in the excision of a 374 bp fragment comprising nucleotides #105-#470 of the human BMP-9 sequence (SEQ ID NO:8) and the additional nucleotides of oligonucleotide primers #3 and #4 which contain the recognition sequences for the restriction endonucleases Apa I and EcoR I. This 374 bp Apa I/EcoR I fragment is combined with the 972 bp Sal I/Apa I fragment from p138 (isolation described above) and ligated to the mammalian cell expression plasmid pED6 (a derivative of pEMC2β1) which has been digested with Sal I and EcoR I. The resulting clone is designated p324.

The clone ML14a (murine BMP-9) is digested with EcoO109 I and Xba I to generate a fragment comprising nucleotides #621-#1515 of SEQ ID NO:1.

The following oligonucleotides are synthesized on an automated DNA synthesizer and combined such that their complimentary sequences can base pair (anneal) with each other to generate a double stranded synthetic DNA linker designated LINK-2;

7 TCGACCACCATGTCCCCTGG (SEQ ID NO:17)

8 GCCCCAGGGGACATGGTGG (SEQ ID NO:18)

This double stranded synthetic DNA linker (LINK-2) anneals in such a way that it generates single stranded ends which are compatible to DNA fragments digested with Sal I (one end) or EcoO109 I (the other end) as indicated below:

7 TCGACCACCATGTCCCCTGG
       GGTGGTACAGGGGACCCCG (SEQ ID NO: 19) #8

This LINK-2 synthetic DNA linker is ligated to the 895 bp EcoO109 I/Xba I fragment comprising nucleotides #621-#1515 of murine BMP-9 (SEQ ID NO:1) described above. This results in a 915 bp Sal I/Xb I fragment.

The clone p324 is digested with Sal I/Xba I to remove sequences comprising nucleotides #6-#56 of LINK-1 (SEQ ID NO: 16) (refer to oligo #5 for location) and nucleotides #621-#1515 of murine BMP-9 (SEQ ID NO:1). The sequences comprising nucleotides #35-#60 of LINK-1 (SEQ ID NO:16) (refer to oligo #5 for location) and the sequences comprising the 374 bp Apa I/EcoR I fragment (human BMP-9 sequences) derived from phBMP9mex-1 remain attached to the pED6 backbone. The 915 bp Sal I/Xba I fragment comprising LINK-2 sequences and nucleotides #621-#1515 of murine BMP-9 (SEQ ID NO:1) is ligated into the p324 clone from which the Sal I to Xba I sequences described above have been removed.

The resulting plasmid is designated BMP9 fusion and comprises LINK-2, nucleotides #621-#1551 of murine BMP-9 (SEQ ID NO:1), nucleotides #35-#59 of LINK-1 (SEQ ID NO:16) (refer to the numbering of oligonucleotide #5), and the 374 bp Apa I/EcoR I fragment (human BMP-9) derived from clone pBMP9max-1 (describe above) inserted between the Sal I and EcoR I sites of the mammalian cell expression vector pED6.

BMP9 fusion is transfected into CHO cells using standard techniques known to those having ordinary skill in the art to create stable cell lines capable of expressing human BMP-9 protein. The cell lines are cultured under suitable culture conditions and the BMP-9 protein is isolated and purified from the culture medium.

EXAMPLE V

Biological Activity of Expressed BMP-9

To measure the biological activity of the expressed BMP-9 proteins obtained in Example IV above, the proteins are recovered from the cell culture and purified by isolating the BMP-9 proteins from other proteinaceous materials with which they are co-produced as well as from other contaminants. The purified protein may be assayed in accordance with the rat bone formation assay described in Example III.

Purification is carried out using standard techniques known to those skilled in the art. It is contemplated, as with other BMP proteins, that purification may include the use of Heparin sepharose.

Protein analysis is conducted using standard techniques such as SDS-PAGE acrylamide [U.K. Laemmli, *Nature* 227: 680 (1970)] stained with silver [R. R. Oakley, et al. *Anal. Biochem.* 105: 361 (1980)] and by immunoblot [H. Towbin, et al. *Proc. Natl. Acad. Sci. USA* 76: 4350 (1979)]

The foregoing descriptions detail presently preferred embodiments of the present invention. Numerous modifications and variations in practice thereof are expected to occur to those skilled in the art upon consideration of these descriptions. Those modifications and variations are believed to be encompassed within the claims appended hereto.

What is claimed is:

1. A purified bone morphogenetic protein-9 (BMP-9) polypeptide consisting of the amino acid sequence from amino acid #8-#110 of SEQ ID NO: 9.

2. A purified bone morphogenetic protein-9 (BMP-9) polypeptide consisting of the amino acid sequence from amino acid #1-#110 of SEQ ID NO: 9.

3. A purified bone morphogenetic protein-9(BMP-9) polypeptide wherein said polypeptide is a dimer wherein each subunit consists of at least the amino acid sequence from amino acid #8-#110 of SEQ ID NO: 9.

4. A purified bone morphogenetic protein-9(BMP-9) polypeptide of wherein said polypeptide is a dimer wherein each subunit consists of at least the amino acid sequence from amino acid #1-#110 of SEQ ID NO: 9.

5. A purified bone morphogenetic protein-9 (BMP-9) produced by the steps of
   (a) culturing a cell transformed with an expression vector containing DNA having the nucleotide sequence from nucleotide #124 to #453 of SEQ ID NO: 8; and
   (b) recovering and purifying from said culture medium a protein consisting of the amino acid sequence from amino acid #1 to amino acid #110 of SEQ ID NO: 9.

6. A purified bone morphogenetic protein-9 (BMP-9) produced by the steps of
   (a) culturing a cell transformed with an expression sector containing DNA having the nucleotide sequence from nucleotide #124 to #453 of SEQ ID NO: 8; and
   (b) recovering from said culture medium a protein consisting of the amino acid sequence from amino acid #8 to amino acid #110 of SEQ ID NO: 9.

7. An isolated DNA sequence encoding a bone morphogenetic protein-9 (BMP-9) selected from the group consisting of:
   (a) nucleotide #124 to #453 of SEQ ID NO: 8;
   (b) nucleotide #145 to #453 of SEQ ID NO:8
   (c) nucleotide #610 to #1896 of SEQ ID NO:1; and
   (d) degenerative sequences of (a) through (c).

8. A host cell transformed with a vector containing a DNA sequence of claim 7.

9. A method for producing a purified bone morphogenetic protein-9 (BMP-9) said method comprising the steps of
   (a) culturing a cell transformed with an expression vector containing a DNA of claim 7; and
   (b) recovering and purifying said BMP-9 protein from the culture medium.

10. A pharmaceutical composition comprising a bone morphogenetic protein-9 (BMP-9)of claim 1, 2, 3 or 4 in admixture with a pharmaceutically acceptable vehicle.

11. A composition of claim 10 further comprising a matrix that supports said composition and provides a surface for bone and/or cartilage growth.

12. The composition of claim 11 wherein said matrix is selected from the group consisting of hydroxyapatite, collagen, polylactic acid and tricalcium phosphate.

13. A method for inducing bone and/or cartilage formation in a patient in need of same comprising administering to said patient an effective amount of the composition of claim 10.

14. A purified mammalian BMP-9 protein produced by the steps of
   (a) culturing a cell transformed with an expression vector containing a DNA consisting of the nucleotide sequence from nucleotide #610 to #1893 of SEQ ID NO:1 and
   (b) recovering and purifying from said culture medium a protein consisting of the amino acid sequence from amino acid #1 to amino acid #110 of SEQ ID NO:2.

* * * * *

SEQUENCE LISTING ( 1 ) GENERAL INFORMATION:

( i i i ) NUMBER OF SEQUENCES: 19

( 2 ) INFORMATION FOR SEQ ID NO:1:

( i ) SEQUENCE CHARACTERISTICS:
        ( A ) LENGTH: 2447 base pairs
        ( B ) TYPE: nucleic acid
        ( C ) STRANDEDNESS: double
        ( D ) TOPOLOGY: linear ( i i ) MOLECULE TYPE: cDNA to mRNA ( i i i ) HYPOTHETICAL: NO ( i v ) ANTI-SENSE: NO ( v i ) ORIGINAL SOURCE:
        ( A ) ORGANISM: Mus musculus
        ( B ) STRAIN: C57B46xCBA
        ( F ) TISSUE TYPE: liver ( v i i ) IMMEDIATE SOURCE:
        ( A ) LIBRARY: Mouse liver cDNA
        ( B ) CLONE: ML14A ( v i i i ) POSITION IN GENOME:
        ( C ) UNITS: bp ( i x ) FEATURE:
        ( A ) NAME/KEY: mat_peptide
        ( B ) LOCATION: 1564..1893

( i x ) FEATURE:
        ( A ) NAME/KEY: CDS
        ( B ) LOCATION: 610..1896

( i x ) FEATURE:
        ( A ) NAME/KEY: mRNA
        ( B ) LOCATION: 1..2447

( x i ) SEQUENCE DESCRIPTION: SEQ ID NO:1:

```
CATTAATAAA  TATTAAGTAT  TGGAATTAGT  GAAATTGGAG  TTCCTTGTGG  AAGGAAGTGG       60

GCAAGTGAGC  TTTTTAGTTT  GTGTCGGAAG  CCTGTAATTA  CGGCTCCAGC  TCATAGTGGA      120

ATGGCTATAC  TTAGATTTAT  GGATAGTTGG  GTAGTAGGTG  TAAATGTATG  TGGTAAAAGG      180

CCTAGGAGAT  TTGTTGATCC  AATAAATATG  ATTAGGGAAA  CAATTATTAG  GGTTCATGTT      240

CGTCCTTTTG  GTGTGTGGAT  TAGCATTATT  TGTTTGATAA  TAAGTTTAAC  TAGTCAGTGT      300

TGGAAAGAAT  GGAGACGGTT  GTTGATTAGG  CGTTTTGAGG  ATGGGAATAG  GATTGAAGGA      360

AATATAATGA  TGGCTACAAC  GATTGGGAAT  CCTATTATTG  TTGGGGTAAT  GAATGAGGCA      420

AATAGATTTT  CGTTCATTTT  AATTCTCAAG  GGGTTTTTAC  TTTTATGTTT  GTTAGTGATA      480

TTGGTGAGTA  GGCCAAGGGT  TAATAGTGTA  ATTGAATTAT  AGTGAAATCA  TATTACTAGA      540
```

```
CCTGATGTTA GAAGGAGGGC TGAAAAGGCT CCTTCCCTCC CAGGACAAAA CCGGAGCAGG                    600

GCCACCCGG ATG TCC CCT GGG GCC TTC CGG GTG GCC CTG CTC CCG CTG                        648
          Met Ser Pro Gly Ala Phe Arg Val Ala Leu Leu Pro Leu
          -318      -315              -310

TTC CTG CTG GTC TGT GTC ACA CAG CAG AAG CCG CTG CAG AAC TGG GAA                      696
Phe Leu Leu Val Cys Val Thr Gln Gln Lys Pro Leu Gln Asn Trp Glu
-305             -300              -295                      -290

CAA GCA TCC CCT GGG GAA AAT GCC CAC AGC TCC CTG GGA TTG TCT GGA                      744
Gln Ala Ser Pro Gly Glu Asn Ala His Ser Ser Leu Gly Leu Ser Gly
                 -285             -280                      -275

GCT GGA GAG GAG GGT GTC TTT GAC CTG CAG ATG TTC CTG GAG AAC ATG                      792
Ala Gly Glu Glu Gly Val Phe Asp Leu Gln Met Phe Leu Glu Asn Met
             -270             -265              -260

AAG GTG GAT TTC CTA CGC AGC CTT AAC CTC AGC GGC ATT CCC TCC CAG                      840
Lys Val Asp Phe Leu Arg Ser Leu Asn Leu Ser Gly Ile Pro Ser Gln
         -255             -250              -245

GAC AAA ACC AGA GCG GAG CCA CCC CAG TAC ATG ATC GAC TTG TAC AAC                      888
Asp Lys Thr Arg Ala Glu Pro Pro Gln Tyr Met Ile Asp Leu Tyr Asn
     -240             -235              -230

AGA TAC ACA ACG GAC AAA TCG TCT ACG CCT GCC TCC AAC ATC GTG CGG                      936
Arg Tyr Thr Thr Asp Lys Ser Ser Thr Pro Ala Ser Asn Ile Val Arg
-225             -220             -215                       -210

AGC TTC AGC GTG GAA GAT GCT ATA TCG ACA GCT GCC ACG GAG GAC TTC                      984
Ser Phe Ser Val Glu Asp Ala Ile Ser Thr Ala Ala Thr Glu Asp Phe
                 -205             -200                      -195

CCC TTT CAG AAG CAC ATC CTG ATC TTC AAC ATC TCC ATC CCG AGG CAC                     1032
Pro Phe Gln Lys His Ile Leu Ile Phe Asn Ile Ser Ile Pro Arg His
             -190             -185              -180

GAG CAG ATC ACC AGG GCT GAG CTC CGA CTC TAT GTC TCC TGC CAA AAT                     1080
Glu Gln Ile Thr Arg Ala Glu Leu Arg Leu Tyr Val Ser Cys Gln Asn
         -175             -170              -165

GAT GTG GAC TCC ACT CAT GGG CTG GAA GGA AGC ATG GTC GTT TAT GAT                     1128
Asp Val Asp Ser Thr His Gly Leu Glu Gly Ser Met Val Val Tyr Asp
     -160             -155              -150

GTT CTG GAG GAC AGT GAG ACT TGG GAC CAG GCC ACG GGG ACC AAG ACC                     1176
Val Leu Glu Asp Ser Glu Thr Trp Asp Gln Ala Thr Gly Thr Lys Thr
-145             -140             -135                       -130

TTC TTG GTA TCC CAG GAC ATT CGG GAC GAA GGA TGG GAG ACT TTA GAA                     1224
Phe Leu Val Ser Gln Asp Ile Arg Asp Glu Gly Trp Glu Thr Leu Glu
                 -125             -120                      -115

GTA TCG AGT GCC GTG AAG CGG TGG GTC AGG GCA GAC TCC ACA ACA AAC                     1272
Val Ser Ser Ala Val Lys Arg Trp Val Arg Ala Asp Ser Thr Thr Asn
             -110             -105              -100

AAA AAT AAG CTC GAG GTG ACA GTG CAG AGC CAC AGG GAG AGC TGT GAC                     1320
Lys Asn Lys Leu Glu Val Thr Val Gln Ser His Arg Glu Ser Cys Asp
         -95              -90                       -85

ACA CTG GAC ATC AGT GTC CCT CCA GGT TCC AAA AAC CTG CCC TTC TTT                     1368
Thr Leu Asp Ile Ser Val Pro Pro Gly Ser Lys Asn Leu Pro Phe Phe
     -80              -75                       -70

GTT GTC TTC TCC AAT GAC CGC AGC AAT GGG ACC AAG GAG ACC AGA CTG                     1416
Val Val Phe Ser Asn Asp Arg Ser Asn Gly Thr Lys Glu Thr Arg Leu
-65              -60                       -55                       -50

GAG CTG AAG GAG ATG ATC GGC CAT GAG CAG GAG ACC ATG CTT GTG AAG                     1464
Glu Leu Lys Glu Met Ile Gly His Glu Gln Glu Thr Met Leu Val Lys
                 -45              -40                       -35

ACA GCC AAA AAT GCT TAC CAG GTG GCA GGT GAG AGC CAA GAG GAG GAG                     1512
Thr Ala Lys Asn Ala Tyr Gln Val Ala Gly Glu Ser Gln Glu Glu Glu
             -30              -25                       -20

GGT CTA GAT GGA TAC ACA GCT GTG GGA CCA CTT TTA GCT AGA AGG AAG                     1560
Gly Leu Asp Gly Tyr Thr Ala Val Gly Pro Leu Leu Ala Arg Arg Lys
```

|   |   |   |   |   |   |   |   |   |   |   |   |   |   |   |   |
|---|---|---|---|---|---|---|---|---|---|---|---|---|---|---|---|
|   | -15 |   |   |   |   |   | -10 |   |   |   |   |   | -5 |   |   |
| AGG | AGC | ACC | GGA | GCC | AGC | AGC | CAC | TGC | CAG | AAG | ACT | TCT | CTC | AGG | GTG | 1608 |
| Arg | Ser | Thr | Gly | Ala | Ser | Ser | His | Cys | Gln | Lys | Thr | Ser | Leu | Arg | Val |
| 1 |   |   |   | 5 |   |   |   |   | 10 |   |   |   |   | 15 |   |
| AAC | TTT | GAG | GAC | ATC | GGC | TGG | GAC | AGC | TGG | ATC | ATT | GCA | CCC | AAG | GAA | 1656 |
| Asn | Phe | Glu | Asp | Ile | Gly | Trp | Asp | Ser | Trp | Ile | Ile | Ala | Pro | Lys | Glu |
|   |   |   | 20 |   |   |   |   | 25 |   |   |   |   | 30 |   |   |
| TAT | GAC | GCC | TAT | GAG | TGT | AAA | GGG | GGT | TGC | TTC | TTC | CCA | TTG | GCT | GAT | 1704 |
| Tyr | Asp | Ala | Tyr | Glu | Cys | Lys | Gly | Gly | Cys | Phe | Phe | Pro | Leu | Ala | Asp |
|   |   | 35 |   |   |   |   | 40 |   |   |   |   | 45 |   |   |
| GAC | GTG | ACA | CCC | ACC | AAA | CAT | GCC | ATC | GTG | CAG | ACC | CTG | GTG | CAT | CTC | 1752 |
| Asp | Val | Thr | Pro | Thr | Lys | His | Ala | Ile | Val | Gln | Thr | Leu | Val | His | Leu |
|   | 50 |   |   |   |   | 55 |   |   |   |   | 60 |   |   |   |   |
| GAG | TTC | CCC | ACA | AAG | GTG | GGC | AAA | GCC | TGC | TGC | GTT | CCC | ACC | AAA | CTG | 1800 |
| Glu | Phe | Pro | Thr | Lys | Val | Gly | Lys | Ala | Cys | Cys | Val | Pro | Thr | Lys | Leu |
| 65 |   |   |   | 70 |   |   |   |   | 75 |   |   |   |   |   |   |
| AGT | CCC | ATC | TCC | ATC | CTC | TAC | AAG | GAT | GAC | ATG | GGG | GTG | CCA | ACC | CTC | 1848 |
| Ser | Pro | Ile | Ser | Ile | Leu | Tyr | Lys | Asp | Asp | Met | Gly | Val | Pro | Thr | Leu |
| 80 |   |   |   | 85 |   |   |   |   | 90 |   |   |   |   | 95 |   |
| AAG | TAC | CAC | TAT | GAG | GGG | ATG | AGT | GTG | GCT | GAG | TGT | GGG | TGT | AGG | TAGTCCCT | 1903 |
| Lys | Tyr | His | Tyr | Glu | Gly | Met | Ser | Val | Ala | Glu | Cys | Gly | Cys | Arg |   |
|   |   |   | 100 |   |   |   |   | 105 |   |   |   |   | 110 |   |   |

```
AGCCACCCAG GGTGGGGATA CAGGACATGG AAGAGGTTCT GGTACGGTCC TGCATCCTCC  1963
TGCGCATGGT ATGCCTAAGT TGATCAGAAA CCATCCTTGA GAAGAAAGG  AGTTAGTTGC  2023
CCTTCTTGTG TCTGGTGGGT CCCTCTGCTG AAGTGACAAT GACTGGGGTA TGCGGGCCTG  2083
TGGGCAGAGC AGGAGACCCT GGAAGGGTTA GTGGGTAGAA AGATGTCAAA AAGGAAGCTG  2143
TGGGTAGATG ACCTGCACTC CAGTGATTAG AAGTCCAGCC TTACCTGTGA GAGAGCTCCT  2203
GGCATCTAAG AGAACTCTGC TTCCTCATCA TCCCCACCGA CTTGTTCTTC CTTGGGAGTG  2263
TGTCCTCAGG GAGAACAGCA TTGCTGTTCC TGTGCCTCAA GCTCCAGCT  GACTCTCCTG  2323
TGGCTCATAG GACTGAATGG GGTGAGGAAG AGCCTGATGC CCTCTGGCAA TCAGAGCCCG  2383
AAGGACTTCA AACATCTGG  ACAACTCTCA TTGACTGATG CTCCAACATA ATTTTTAAAA  2443
AGAG                                                                2447
```

( 2 ) INFORMATION FOR SEQ ID NO:2:

( i ) SEQUENCE CHARACTERISTICS:
        ( A ) LENGTH: 428 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

|   |   |   |   |   |   |   |   |   |   |   |   |   |   |   |
|---|---|---|---|---|---|---|---|---|---|---|---|---|---|---|
| Met | Ser | Pro | Gly | Ala | Phe | Arg | Val | Ala | Leu | Leu | Pro | Leu | Phe | Leu | Leu |
| -318 |   |   | -315 |   |   |   |   | -310 |   |   |   |   | -305 |   |   |
| Val | Cys | Val | Thr | Gln | Gln | Lys | Pro | Leu | Gln | Asn | Trp | Glu | Gln | Ala | Ser |
|   |   | -300 |   |   |   |   | -295 |   |   |   |   | -290 |   |   |   |
| Pro | Gly | Glu | Asn | Ala | His | Ser | Ser | Leu | Gly | Leu | Ser | Gly | Ala | Gly | Glu |
|   |   | -285 |   |   |   |   | -280 |   |   |   |   | -275 |   |   |   |
| Glu | Gly | Val | Phe | Asp | Leu | Gln | Met | Phe | Leu | Glu | Asn | Met | Lys | Val | Asp |
| -270 |   |   |   |   | -265 |   |   |   |   | -260 |   |   |   |   | -255 |
| Phe | Leu | Arg | Ser | Leu | Asn | Leu | Ser | Gly | Ile | Pro | Ser | Gln | Asp | Lys | Thr |
|   |   |   |   | -250 |   |   |   |   | -245 |   |   |   |   | -240 |   |
| Arg | Ala | Glu | Pro | Pro | Gln | Tyr | Met | Ile | Asp | Leu | Tyr | Asn | Arg | Tyr | Thr |
|   |   |   |   | -235 |   |   |   |   | -230 |   |   |   |   | -225 |   |

```
Thr  Asp  Lys  Ser  Ser  Thr  Pro  Ala  Ser  Asn  Ile  Val  Arg  Ser  Phe  Ser
         -220                -215                     -210

Val  Glu  Asp  Ala  Ile  Ser  Thr  Ala  Ala  Thr  Glu  Asp  Phe  Pro  Phe  Gln
    -205                -200                     -195

Lys  His  Ile  Leu  Ile  Phe  Asn  Ile  Ser  Ile  Pro  Arg  His  Glu  Gln  Ile
-190                -185                     -180                          -175

Thr  Arg  Ala  Glu  Leu  Arg  Leu  Tyr  Val  Ser  Cys  Gln  Asn  Asp  Val  Asp
              -170                -165                          -160

Ser  Thr  His  Gly  Leu  Glu  Gly  Ser  Met  Val  Val  Tyr  Asp  Val  Leu  Glu
              -155                -150                          -145

Asp  Ser  Glu  Thr  Trp  Asp  Gln  Ala  Thr  Gly  Thr  Lys  Thr  Phe  Leu  Val
         -140                -135                     -130

Ser  Gln  Asp  Ile  Arg  Asp  Glu  Gly  Trp  Glu  Thr  Leu  Glu  Val  Ser  Ser
    -125                -120                          -115

Ala  Val  Lys  Arg  Trp  Val  Arg  Ala  Asp  Ser  Thr  Thr  Asn  Lys  Asn  Lys
-110                -105                     -100                          -95

Leu  Glu  Val  Thr  Val  Gln  Ser  His  Arg  Glu  Ser  Cys  Asp  Thr  Leu  Asp
              -90                 -85                           -80

Ile  Ser  Val  Pro  Pro  Gly  Ser  Lys  Asn  Leu  Pro  Phe  Phe  Val  Val  Phe
              -75                 -70                           -65

Ser  Asn  Asp  Arg  Ser  Asn  Gly  Thr  Lys  Glu  Thr  Arg  Leu  Glu  Leu  Lys
         -60                 -55                      -50

Glu  Met  Ile  Gly  His  Glu  Gln  Glu  Thr  Met  Leu  Val  Lys  Thr  Ala  Lys
    -45                 -40                           -35

Asn  Ala  Tyr  Gln  Val  Ala  Gly  Glu  Ser  Gln  Glu  Glu  Gly  Leu  Asp
-30                      -25                 -20                           -15

Gly  Tyr  Thr  Ala  Val  Gly  Pro  Leu  Leu  Ala  Arg  Arg  Lys  Arg  Ser  Thr
              -10                 -5                                       1

Gly  Ala  Ser  Ser  His  Cys  Gln  Lys  Thr  Ser  Leu  Arg  Val  Asn  Phe  Glu
         5                        10                      15

Asp  Ile  Gly  Trp  Asp  Ser  Trp  Ile  Ile  Ala  Pro  Lys  Glu  Tyr  Asp  Ala
    20                      25                      30

Tyr  Glu  Cys  Lys  Gly  Gly  Cys  Phe  Phe  Pro  Leu  Ala  Asp  Asp  Val  Thr
35                       40                      45                           50

Pro  Thr  Lys  His  Ala  Ile  Val  Gln  Thr  Leu  Val  His  Leu  Glu  Phe  Pro
              55                       60                      65

Thr  Lys  Val  Gly  Lys  Ala  Cys  Cys  Val  Pro  Thr  Lys  Leu  Ser  Pro  Ile
              70                       75                      80

Ser  Ile  Leu  Tyr  Lys  Asp  Asp  Met  Gly  Val  Pro  Thr  Leu  Lys  Tyr  His
              85                       90                      95

Tyr  Glu  Gly  Met  Ser  Val  Ala  Glu  Cys  Gly  Cys  Arg
    100                      105                     110
```

( 2 ) INFORMATION FOR SEQ ID NO:3:

( i ) SEQUENCE CHARACTERISTICS:
        ( A ) LENGTH: 1954 base pairs
        ( B ) TYPE: nucleic acid
        ( C ) STRANDEDNESS: double
        ( D ) TOPOLOGY: linear ( i i ) MOLECULE TYPE: cDNA to mRNA ( i i i ) HYPOTHETICAL: NO ( i v ) ANTI-SENSE: NO ( v i ) ORIGINAL SOURCE:
        ( A ) ORGANISM: Homo sapiens (G) CELL TYPE: Osteosarcoma Cell Line
(H) CELL LINE: U-2OS (vii) IMMEDIATE SOURCE:
(A) LIBRARY: U2OS cDNA in Lambda gt10
(B) CLONE: Lambda U2OS-3

(viii) POSITION IN GENOME:
(C) UNITS: bp (ix) FEATURE:
(A) NAME/KEY: CDS
(B) LOCATION: 403..1629

(ix) FEATURE:
(A) NAME/KEY: mat_peptide
(B) LOCATION: 1279..1626

(ix) FEATURE:
(A) NAME/KEY: mRNA
(B) LOCATION: 9..1934

(xi) SEQUENCE DESCRIPTION: SEQ ID NO:3:

```
CTCTAGAGGG CAGAGGAGGA GGGAGGGAGG GAAGGAGCGC GGAGCCCGGC CCGGAAGCTA        60

GGTGAGTGTG GCATCCGAGC TGAGGGACGC GAGCCTGAGA CGCCGCTGCT GCTCCGGCTG       120

AGTATCTAGC TTGTCTCCCC GATGGGATTC CCGTCCAAGC TATCTCGAGC CTGCAGCGCC       180

ACAGTCCCCG GCCCTCGCCC AGGTTCACTG CAACCGTTCA GAGGTCCCCA GGAGCTGCTG       240

CTGGCGAGCC CGCTACTGCA GGGACCTATG GAGCCATTCC GTAGTGCCAT CCCGAGCAAC       300

GCACTGCTGC AGCTTCCCTG AGCCTTTCCA GCAAGTTTGT TCAAGATTGG CTGTCAAGAA       360

TCATGGACTG TTATTATATG CCTTGTTTTC TGTCAAGACA CC ATG ATT CCT GGT         414
                                              Met Ile Pro Gly
                                              -292       -290

AAC CGA ATG CTG ATG GTC GTT TTA TTA TGC CAA GTC CTG CTA GGA GGC         462
Asn Arg Met Leu Met Val Val Leu Leu Cys Gln Val Leu Leu Gly Gly
        -285                -280                    -275

GCG AGC CAT GCT AGT TTG ATA CCT GAG ACG GGG AAG AAA AAA GTC GCC         510
Ala Ser His Ala Ser Leu Ile Pro Glu Thr Gly Lys Lys Lys Val Ala
        -270                -265                    -260

GAG ATT CAG GGC CAC GCG GGA GGA CGC CGC TCA GGG CAG AGC CAT GAG         558
Glu Ile Gln Gly His Ala Gly Gly Arg Arg Ser Gly Gln Ser His Glu
-255                -250                    -245

CTC CTG CGG GAC TTC GAG GCG ACA CTT CTG CAG ATG TTT GGG CTG CGC         606
Leu Leu Arg Asp Phe Glu Ala Thr Leu Leu Gln Met Phe Gly Leu Arg
-240                -235                    -230                -225

CGC CGC CCG CAG CCT AGC AAG AGT GCC GTC ATT CCG GAC TAC ATG CGG         654
Arg Arg Pro Gln Pro Ser Lys Ser Ala Val Ile Pro Asp Tyr Met Arg
            -220                    -215                -210

GAT CTT TAC CGG CTT CAG TCT GGG GAG GAG GAG GAA GAG CAG ATC CAC         702
Asp Leu Tyr Arg Leu Gln Ser Gly Glu Glu Glu Glu Glu Gln Ile His
        -205                -200                    -195

AGC ACT GGT CTT GAG TAT CCT GAG CGC CCG GCC AGC CGG GCC AAC ACC         750
Ser Thr Gly Leu Glu Tyr Pro Glu Arg Pro Ala Ser Arg Ala Asn Thr
        -190                -185                    -180

GTG AGG AGC TTC CAC CAC GAA GAA CAT CTG GAG AAC ATC CCA GGG ACC         798
Val Arg Ser Phe His His Glu Glu His Leu Glu Asn Ile Pro Gly Thr
    -175                -170                    -165

AGT GAA AAC TCT GCT TTT CGT TTC CTC TTT AAC CTC AGC AGC ATC CCT         846
Ser Glu Asn Ser Ala Phe Arg Phe Leu Phe Asn Leu Ser Ser Ile Pro
-160                -155                    -150                -145

GAG AAC GAG GTG ATC TCC TCT GCA GAG CTT CGG CTC TTC CGG GAG CAG         894
Glu Asn Glu Val Ile Ser Ser Ala Glu Leu Arg Leu Phe Arg Glu Gln
            -140                    -135                    -130
```

| | | | | | | | | | | | | | | | | |
|---|---|---|---|---|---|---|---|---|---|---|---|---|---|---|---|---|
| GTG | GAC | CAG | GGC | CCT | GAT | TGG | GAA | AGG | GGC | TTC | CAC | CGT | ATA | AAC | ATT | 942 |
| Val | Asp | Gln | Gly | Pro | Asp | Trp | Glu | Arg | Gly | Phe | His | Arg | Ile | Asn | Ile | |
| | | -125 | | | | -120 | | | | | | | -115 | | | |
| TAT | GAG | GTT | ATG | AAG | CCC | CCA | GCA | GAA | GTG | GTG | CCT | GGG | CAC | CTC | ATC | 990 |
| Tyr | Glu | Val | Met | Lys | Pro | Pro | Ala | Glu | Val | Val | Pro | Gly | His | Leu | Ile | |
| | | -110 | | | | -105 | | | | | -100 | | | | | |
| ACA | CGA | CTA | CTG | GAC | ACG | AGA | CTG | GTC | CAC | CAC | AAT | GTG | ACA | CGG | TGG | 1038 |
| Thr | Arg | Leu | Leu | Asp | Thr | Arg | Leu | Val | His | His | Asn | Val | Thr | Arg | Trp | |
| | -95 | | | | | -90 | | | | | -85 | | | | | |
| GAA | ACT | TTT | GAT | GTG | AGC | CCT | GCG | GTC | CTT | CGC | TGG | ACC | CGG | GAG | AAG | 1086 |
| Glu | Thr | Phe | Asp | Val | Ser | Pro | Ala | Val | Leu | Arg | Trp | Thr | Arg | Glu | Lys | |
| -80 | | | | | -75 | | | | | -70 | | | | | -65 | |
| CAG | CCA | AAC | TAT | GGG | CTA | GCC | ATT | GAG | GTG | ACT | CAC | CTC | CAT | CAG | ACT | 1134 |
| Gln | Pro | Asn | Tyr | Gly | Leu | Ala | Ile | Glu | Val | Thr | His | Leu | His | Gln | Thr | |
| | | | -60 | | | | | -55 | | | | | | -50 | | |
| CGG | ACC | CAC | CAG | GGC | CAG | CAT | GTC | AGG | ATT | AGC | CGA | TCG | TTA | CCT | CAA | 1182 |
| Arg | Thr | His | Gln | Gly | Gln | His | Val | Arg | Ile | Ser | Arg | Ser | Leu | Pro | Gln | |
| | | | -45 | | | | | -40 | | | | | | -35 | | |
| GGG | AGT | GGG | AAT | TGG | GCC | CAG | CTC | CGG | CCC | CTC | CTG | GTC | ACC | TTT | GGC | 1230 |
| Gly | Ser | Gly | Asn | Trp | Ala | Gln | Leu | Arg | Pro | Leu | Leu | Val | Thr | Phe | Gly | |
| | | -30 | | | | | -25 | | | | | | -20 | | | |
| CAT | GAT | GGC | CGG | GGC | CAT | GCC | TTG | ACC | CGA | CGC | CGG | AGG | GCC | AAG | CGT | 1278 |
| His | Asp | Gly | Arg | Gly | His | Ala | Leu | Thr | Arg | Arg | Arg | Arg | Ala | Lys | Arg | |
| | -15 | | | | | | -10 | | | | | | -5 | | | |
| AGC | CCT | AAG | CAT | CAC | TCA | CAG | CGG | GCC | AGG | AAG | AAG | AAT | AAG | AAC | TGC | 1326 |
| Ser | Pro | Lys | His | His | Ser | Gln | Arg | Ala | Arg | Lys | Lys | Asn | Lys | Asn | Cys | |
| 1 | | | | 5 | | | | | 10 | | | | | 15 | | |
| CGG | CGC | CAC | TCG | CTC | TAT | GTG | GAC | TTC | AGC | GAT | GTG | GGC | TGG | AAT | GAC | 1374 |
| Arg | Arg | His | Ser | Leu | Tyr | Val | Asp | Phe | Ser | Asp | Val | Gly | Trp | Asn | Asp | |
| | | | 20 | | | | | 25 | | | | | 30 | | | |
| TGG | ATT | GTG | GCC | CCA | CCA | GGC | TAC | CAG | GCC | TTC | TAC | TGC | CAT | GGG | GAC | 1422 |
| Trp | Ile | Val | Ala | Pro | Pro | Gly | Tyr | Gln | Ala | Phe | Tyr | Cys | His | Gly | Asp | |
| | | 35 | | | | | 40 | | | | | 45 | | | | |
| TGC | CCC | TTT | CCA | CTG | GCT | GAC | CAC | CTC | AAC | TCA | ACC | AAC | CAT | GCC | ATT | 1470 |
| Cys | Pro | Phe | Pro | Leu | Ala | Asp | His | Leu | Asn | Ser | Thr | Asn | His | Ala | Ile | |
| | 50 | | | | | 55 | | | | | 60 | | | | | |
| GTG | CAG | ACC | CTG | GTC | AAT | TCT | GTC | AAT | TCC | AGT | ATC | CCC | AAA | GCC | TGT | 1518 |
| Val | Gln | Thr | Leu | Val | Asn | Ser | Val | Asn | Ser | Ser | Ile | Pro | Lys | Ala | Cys | |
| 65 | | | | | 70 | | | | | 75 | | | | | 80 | |
| TGT | GTG | CCC | ACT | GAA | CTG | AGT | GCC | ATC | TCC | ATG | CTG | TAC | CTG | GAT | GAG | 1566 |
| Cys | Val | Pro | Thr | Glu | Leu | Ser | Ala | Ile | Ser | Met | Leu | Tyr | Leu | Asp | Glu | |
| | | | | 85 | | | | | 90 | | | | | 95 | | |
| TAT | GAT | AAG | GTG | GTA | CTG | AAA | AAT | TAT | CAG | GAG | ATG | GTA | GTA | GAG | GGA | 1614 |
| Tyr | Asp | Lys | Val | Val | Leu | Lys | Asn | Tyr | Gln | Glu | Met | Val | Val | Glu | Gly | |
| | | | 100 | | | | | 105 | | | | | 110 | | | |
| TGT | GGG | TGC | CGC | TGAGATCAGG | | CAGTCCTTGA | | GGATAGACAG | | ATATACACAC | | | | | | 1666 |
| Cys | Gly | Cys | Arg | | | | | | | | | | | | | |
| | | 115 | | | | | | | | | | | | | | |

| | | | | |
|---|---|---|---|---|
| CACACACACA | CACCACATAC | ACCACACACA | CACGTTCCCA | TCCACTCACC | CACACACTAC | 1726 |
| ACAGACTGCT | TCCTTATAGC | TGGACTTTTA | TTTAAAAAAA | AAAAAAAAAA | AATGGAAAAA | 1786 |
| ATCCCTAAAC | ATTCACCTTG | ACCTTATTTA | TGACTTTACG | TGCAAATGTT | TTGACCATAT | 1846 |
| TGATCATATA | TTTTGACAAA | ATATATTTAT | AACTACGTAT | TAAAGAAAA | AAATAAAATG | 1906 |
| AGTCATTATT | TTAAAAAAA | AAAAAAAACT | CTAGAGTCGA | CGGAATTC | | 1954 |

( 2 ) INFORMATION FOR SEQ ID NO:4:

( i ) SEQUENCE CHARACTERISTICS:
( A ) LENGTH: 408 amino acids
( B ) TYPE: amino acid ( D ) TOPOLOGY: linear ( i i ) MOLECULE TYPE: protein ( x i ) SEQUENCE DESCRIPTION: SEQ ID NO:4:

```
Met  Ile  Pro  Gly  Asn  Arg  Met  Leu  Met  Val  Val  Leu  Leu  Cys  Gln  Val
-292      -290                -285                    -280

Leu  Leu  Gly  Gly  Ala  Ser  His  Ala  Ser  Leu  Ile  Pro  Glu  Thr  Gly  Lys
     -275                -270                    -265

Lys  Lys  Val  Ala  Glu  Ile  Gln  Gly  His  Ala  Gly  Gly  Arg  Arg  Ser  Gly
-260                -255                    -250                              -245

Gln  Ser  His  Glu  Leu  Leu  Arg  Asp  Phe  Glu  Ala  Thr  Leu  Leu  Gln  Met
               -240                    -235                         -230

Phe  Gly  Leu  Arg  Arg  Arg  Pro  Gln  Pro  Ser  Lys  Ser  Ala  Val  Ile  Pro
               -225                    -220                         -215

Asp  Tyr  Met  Arg  Asp  Leu  Tyr  Arg  Leu  Gln  Ser  Gly  Glu  Glu  Glu  Glu
               -210                    -205                         -200

Glu  Gln  Ile  His  Ser  Thr  Gly  Leu  Glu  Tyr  Pro  Glu  Arg  Pro  Ala  Ser
     -195                    -190                         -185

Arg  Ala  Asn  Thr  Val  Arg  Ser  Phe  His  His  Glu  Glu  His  Leu  Glu  Asn
-180                    -175                         -170                    -165

Ile  Pro  Gly  Thr  Ser  Glu  Asn  Ser  Ala  Phe  Arg  Phe  Leu  Phe  Asn  Leu
                    -160                    -155                         -150

Ser  Ser  Ile  Pro  Glu  Asn  Glu  Val  Ile  Ser  Ser  Ala  Glu  Leu  Arg  Leu
               -145                    -140                         -135

Phe  Arg  Glu  Gln  Val  Asp  Gln  Gly  Pro  Asp  Trp  Glu  Arg  Gly  Phe  His
          -130                    -125                         -120

Arg  Ile  Asn  Ile  Tyr  Glu  Val  Met  Lys  Pro  Pro  Ala  Glu  Val  Val  Pro
     -115                    -110                         -105

Gly  His  Leu  Ile  Thr  Arg  Leu  Leu  Asp  Thr  Arg  Leu  Val  His  His  Asn
-100                    -95                     -90                         -85

Val  Thr  Arg  Trp  Glu  Thr  Phe  Asp  Val  Ser  Pro  Ala  Val  Leu  Arg  Trp
               -80                     -75                          -70

Thr  Arg  Glu  Lys  Gln  Pro  Asn  Tyr  Gly  Leu  Ala  Ile  Glu  Val  Thr  His
               -65                     -60                          -55

Leu  His  Gln  Thr  Arg  Thr  His  Gln  Gly  Gln  His  Val  Arg  Ile  Ser  Arg
               -50                     -45                          -40

Ser  Leu  Pro  Gln  Gly  Ser  Gly  Asn  Trp  Ala  Gln  Leu  Arg  Pro  Leu  Leu
               -35                     -30                          -25

Val  Thr  Phe  Gly  His  Asp  Gly  Arg  Gly  His  Ala  Leu  Thr  Arg  Arg  Arg
-20                      -15                         -10                      -5

Arg  Ala  Lys  Arg  Ser  Pro  Lys  His  His  Ser  Gln  Arg  Ala  Arg  Lys  Lys
                     1              5                          10

Asn  Lys  Asn  Cys  Arg  Arg  His  Ser  Leu  Tyr  Val  Asp  Phe  Ser  Asp  Val
          15                     20                     25

Gly  Trp  Asn  Asp  Trp  Ile  Val  Ala  Pro  Pro  Gly  Tyr  Gln  Ala  Phe  Tyr
     30                     35                     40

Cys  His  Gly  Asp  Cys  Pro  Phe  Pro  Leu  Ala  Asp  His  Leu  Asn  Ser  Thr
45                     50                     55                          60

Asn  His  Ala  Ile  Val  Gln  Thr  Leu  Val  Asn  Ser  Val  Asn  Ser  Ser  Ile
               65                     70                          75

Pro  Lys  Ala  Cys  Cys  Val  Pro  Thr  Glu  Leu  Ser  Ala  Ile  Ser  Met  Leu
               80                     85                          90

Tyr  Leu  Asp  Glu  Tyr  Asp  Lys  Val  Val  Leu  Lys  Asn  Tyr  Gln  Glu  Met
          95                     100                         105
```

Val Val Glu Gly Cys Gly Cys Arg
110                          115

( 2 ) INFORMATION FOR SEQ ID NO:5:

( i ) SEQUENCE CHARACTERISTICS:
        ( A ) LENGTH: 15 base pairs
        ( B ) TYPE: nucleic acid
        ( C ) STRANDEDNESS: double
        ( D ) TOPOLOGY: linear ( i i ) MOLECULE TYPE: cDNA to mRNA ( x i ) SEQUENCE DESCRIPTION: SEQ ID NO:5:

CATGGGCAGC TCGAG                                                                 15

( 2 ) INFORMATION FOR SEQ ID NO:6:

( i ) SEQUENCE CHARACTERISTICS:
        ( A ) LENGTH: 34 base pairs
        ( B ) TYPE: nucleic acid
        ( C ) STRANDEDNESS: double
        ( D ) TOPOLOGY: linear ( i i ) MOLECULE TYPE: cDNA to mRNA ( x i ) SEQUENCE DESCRIPTION: SEQ ID NO:6:

CTGCAGGCGA GCCTGAATTC CTCGAGCCAT CATG                                             34

( 2 ) INFORMATION FOR SEQ ID NO:7:

( i ) SEQUENCE CHARACTERISTICS:
        ( A ) LENGTH: 68 base pairs
        ( B ) TYPE: nucleic acid
        ( C ) STRANDEDNESS: double
        ( D ) TOPOLOGY: linear ( i i ) MOLECULE TYPE: cDNA to mRNA ( x i ) SEQUENCE DESCRIPTION: SEQ ID NO:7:

CGAGGTTAAA AAACGTCTAG GCCCCCCGAA CCACGGGGAC GTGGTTTTCC TTTGAAAAAC                 60

ACGATTGC                                                                          68

( 2 ) INFORMATION FOR SEQ ID NO:8:

( i ) SEQUENCE CHARACTERISTICS:
        ( A ) LENGTH: 470 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( v ) FRAGMENT TYPE: C-terminal ( v i ) ORIGINAL SOURCE:
        ( A ) ORGANISM: Homo sapiens
        ( H ) CELL LINE: W138 (genomic DNA)

( v i i ) IMMEDIATE SOURCE:
        ( A ) LIBRARY: human genomic library
        ( B ) CLONE: lambda 111-1

( v i i i ) POSITION IN GENOME:
        ( C ) UNITS: bp ( i x ) FEATURE:
        ( A ) NAME/KEY: exon
        ( B ) LOCATION: 1..470

(ix) FEATURE:
    (A) NAME/KEY: CDS
    (B) LOCATION: 1..456

(ix) FEATURE:
    (A) NAME/KEY: mat_peptide
    (B) LOCATION: 124..453

(ix) FEATURE:
    (A) NAME/KEY: mRNA
    (B) LOCATION: 1..470

(xi) SEQUENCE DESCRIPTION: SEQ ID NO:8:

```
TGA  ACA  AGA  GAG  TGC  TCA  AGA  AGC  TGT  CCA  AGG  ACG  GCT  CCA  CAG  AGG      48
 *   Thr  Arg  Glu  Cys  Ser  Arg  Ser  Cys  Pro  Arg  Thr  Ala  Pro  Gln  Arg
-41  -40                      -35                      -30

CAG  GTG  AGA  GCA  GTC  ACG  AGG  AGG  ACA  CGG  ATG  GCG  CAC  GTG  GCT  GCG      96
Gln  Val  Arg  Ala  Val  Thr  Arg  Arg  Thr  Arg  Met  Ala  His  Val  Ala  Ala
-25                 -20                      -15                           -10

GGG  TCG  ACT  TTA  GCC  AGG  CGG  AAA  AGG  AGC  GCC  GGG  GCT  GGC  AGC  CAC     144
Gly  Ser  Thr  Leu  Ala  Arg  Arg  Lys  Arg  Ser  Ala  Gly  Ala  Gly  Ser  His
               -5                     1                     5

TGT  CAA  AAG  ACC  TCC  CTG  CGG  GTA  AAC  TTC  GAG  GAC  ATC  GGC  TGG  GAC     192
Cys  Gln  Lys  Thr  Ser  Leu  Arg  Val  Asn  Phe  Glu  Asp  Ile  Gly  Trp  Asp
          10                     15                     20

AGC  TGG  ATC  ATT  GCA  CCC  AAG  GAG  TAT  GAA  GCC  TAC  GAG  TGT  AAG  GGC     240
Ser  Trp  Ile  Ile  Ala  Pro  Lys  Glu  Tyr  Glu  Ala  Tyr  Glu  Cys  Lys  Gly
     25                      30                     35

GGC  TGC  TTC  TTC  CCC  TTG  GCT  GAC  GAT  GTG  ACG  CCG  ACG  AAA  CAC  GCT     288
Gly  Cys  Phe  Phe  Pro  Leu  Ala  Asp  Asp  Val  Thr  Pro  Thr  Lys  His  Ala
 40                      45                     50                          55

ATC  GTG  CAG  ACC  CTG  GTG  CAT  CTC  AAG  TTC  CCC  ACA  AAG  GTG  GGC  AAG     336
Ile  Val  Gln  Thr  Leu  Val  His  Leu  Lys  Phe  Pro  Thr  Lys  Val  Gly  Lys
                    60                      65                          70

GCC  TGC  TGT  GTG  CCC  ACC  AAA  CTG  AGC  CCC  ATC  TCC  GTC  CTC  TAC  AAG     384
Ala  Cys  Cys  Val  Pro  Thr  Lys  Leu  Ser  Pro  Ile  Ser  Val  Leu  Tyr  Lys
               75                      80                          85

GAT  GAC  ATG  GGG  GTG  CCC  ACC  CTC  AAG  TAC  CAT  TAC  GAG  GGC  ATG  AGC     432
Asp  Asp  Met  Gly  Val  Pro  Thr  Leu  Lys  Tyr  His  Tyr  Glu  Gly  Met  Ser
          90                      95                     100

GTG  GCA  GAG  TGT  GGG  TGC  AGG  TAGTATCTGC  CTGCGGG                             470
Val  Ala  Glu  Cys  Gly  Cys  Arg
          105                 110
```

(2) INFORMATION FOR SEQ ID NO:9:

(i) SEQUENCE CHARACTERISTICS:
        (A) LENGTH: 150 amino acids
        (B) TYPE: amino acid
        (D) TOPOLOGY: linear (ii) MOLECULE TYPE: protein (xi) SEQUENCE DESCRIPTION: SEQ ID NO:9:

```
Thr  Arg  Glu  Cys  Ser  Arg  Ser  Cys  Pro  Arg  Thr  Ala  Pro  Gln  Arg
-40                      -35                      -30

Gln  Val  Arg  Ala  Val  Thr  Arg  Arg  Thr  Arg  Met  Ala  His  Val  Ala  Ala
-25                 -20                      -15                           -10

Gly  Ser  Thr  Leu  Ala  Arg  Arg  Lys  Arg  Ser  Ala  Gly  Ala  Gly  Ser  His
               -5                     1                     5

Cys  Gln  Lys  Thr  Ser  Leu  Arg  Val  Asn  Phe  Glu  Asp  Ile  Gly  Trp  Asp
          10                     15                     20

Ser  Trp  Ile  Ile  Ala  Pro  Lys  Glu  Tyr  Glu  Ala  Tyr  Glu  Cys  Lys  Gly
```

|  | 25 |  |  |  | 30 |  |  |  | 35 |  |  |  |
|---|---|---|---|---|---|---|---|---|---|---|---|---|
| Gly | Cys | Phe | Phe | Pro | Leu | Ala | Asp | Asp | Val | Thr | Pro | Thr | Lys | His | Ala |
| 40 |  |  |  | 45 |  |  |  | 50 |  |  |  | 55 |

Gly Cys Phe Phe Pro Leu Ala Asp Asp Val Thr Pro Thr Lys His Ala
40                      45                  50                  55

Ile Val Gln Thr Leu Val His Leu Lys Phe Pro Thr Lys Val Gly Lys
                    60                  65                  70

Ala Cys Cys Val Pro Thr Lys Leu Ser Pro Ile Ser Val Leu Tyr Lys
            75                  80                  85

Asp Asp Met Gly Val Pro Thr Leu Lys Tyr His Tyr Glu Gly Met Ser
        90                  95              100

Val Ala Glu Cys Gly Cys Arg
    105             110

( 2 ) INFORMATION FOR SEQ ID NO:10:

( i ) SEQUENCE CHARACTERISTICS:
        ( A ) LENGTH: 40 base pairs
        ( B ) TYPE: nucleic acid
        ( C ) STRANDEDNESS: double
        ( D ) TOPOLOGY: linear ( i i ) MOLECULE TYPE: cDNA to mRNA ( x i ) SEQUENCE DESCRIPTION: SEQ ID NO:10:

CTATGAGTGT AAAGGGGGTT GCTTCTTCCC ATTGGCTGAT    40

( 2 ) INFORMATION FOR SEQ ID NO:11:

( i ) SEQUENCE CHARACTERISTICS:
        ( A ) LENGTH: 40 base pairs
        ( B ) TYPE: nucleic acid
        ( C ) STRANDEDNESS: double
        ( D ) TOPOLOGY: linear ( i i ) MOLECULE TYPE: cDNA to mRNA ( x i ) SEQUENCE DESCRIPTION: SEQ ID NO:11:

GTGCCAACCC TCAAGTACCA CTATGAGGGG ATGAGTGTGG    40

( 2 ) INFORMATION FOR SEQ ID NO:12:

( i ) SEQUENCE CHARACTERISTICS:
        ( A ) LENGTH: 32 base pairs
        ( B ) TYPE: nucleic acid
        ( C ) STRANDEDNESS: double
        ( D ) TOPOLOGY: linear ( i i ) MOLECULE TYPE: cDNA to mRNA ( x i ) SEQUENCE DESCRIPTION: SEQ ID NO:12:

ATCGGGCCCC TTTTAGCCAG GCGGAAAAGG AG    32

( 2 ) INFORMATION FOR SEQ ID NO:13:

( i ) SEQUENCE CHARACTERISTICS:
        ( A ) LENGTH: 30 base pairs
        ( B ) TYPE: nucleic acid
        ( C ) STRANDEDNESS: double
        ( D ) TOPOLOGY: linear ( i i ) MOLECULE TYPE: cDNA to mRNA ( x i ) SEQUENCE DESCRIPTION: SEQ ID NO:13:

AGCGAATTCC CCGCAGGCAG ATACTACCTG    30

( 2 ) INFORMATION FOR SEQ ID NO:14:

( i ) SEQUENCE CHARACTERISTICS:
    ( A ) LENGTH: 61 base pairs
    ( B ) TYPE: nucleic acid
    ( C ) STRANDEDNESS: double
    ( D ) TOPOLOGY: linear ( i i ) MOLECULE TYPE: cDNA to mRNA ( x i ) SEQUENCE DESCRIPTION: SEQ ID NO:14:

GATTCCGTCG ACCACCATGT CCCCTGGGGC CTGGTCTAGA TGGATACACA GCTGTGGGGC    60
C    61

( 2 ) INFORMATION FOR SEQ ID NO:15:

( i ) SEQUENCE CHARACTERISTICS:
    ( A ) LENGTH: 52 base pairs
    ( B ) TYPE: nucleic acid
    ( C ) STRANDEDNESS: double
    ( D ) TOPOLOGY: linear ( i i ) MOLECULE TYPE: cDNA to mRNA ( x i ) SEQUENCE DESCRIPTION: SEQ ID NO:15:

CCACAGCTGT GTATCCATCT AGACCAGGCC CCAGGGGACA TGGTGGTCGA CG    52

( 2 ) INFORMATION FOR SEQ ID NO:16:

( i ) SEQUENCE CHARACTERISTICS:
    ( A ) LENGTH: 113 base pairs
    ( B ) TYPE: nucleic acid
    ( C ) STRANDEDNESS: double
    ( D ) TOPOLOGY: linear ( i i ) MOLECULE TYPE: cDNA to mRNA ( x i ) SEQUENCE DESCRIPTION: SEQ ID NO:16:

GATTCCGTCG ACCACCATGT CCCCTGGGGC CTGGTCTAGA TGGATACACA GCTGTGGGGC    60
CGCAGCTGGT GGTACAGGGG ACCCCGGACC AGATCTACCT ATGTGTCGAC ACC    113

( 2 ) INFORMATION FOR SEQ ID NO:17:

( i ) SEQUENCE CHARACTERISTICS:
    ( A ) LENGTH: 20 base pairs
    ( B ) TYPE: nucleic acid
    ( C ) STRANDEDNESS: double
    ( D ) TOPOLOGY: linear ( i i ) MOLECULE TYPE: cDNA to mRNA ( x i ) SEQUENCE DESCRIPTION: SEQ ID NO:17:

TCGACCACCA TGTCCCCTGG    20

( 2 ) INFORMATION FOR SEQ ID NO:18:

( i ) SEQUENCE CHARACTERISTICS:
    ( A ) LENGTH: 19 base pairs
    ( B ) TYPE: nucleic acid
    ( C ) STRANDEDNESS: double
    ( D ) TOPOLOGY: linear ( i i ) MOLECULE TYPE: cDNA to mRNA ( x i ) SEQUENCE DESCRIPTION: SEQ ID NO:18:

GCCCCAGGGG ACATGGTGG    19

( 2 ) INFORMATION FOR SEQ ID NO:19:

( i ) SEQUENCE CHARACTERISTICS:

(A) LENGTH: 39 base pairs
(B) TYPE: nucleic acid
(C) STRANDEDNESS: double
(D) TOPOLOGY: linear (ii) MOLECULE TYPE: cDNA to mRNA (xi) SEQUENCE DESCRIPTION: SEQ ID NO:19:

TCGACCACCA TGTCCCCTGG GGTGGTACAG GGGACCCCG      39